United States Patent

Suami

Patent Number: 4,472,379

Date of Patent: Sep. 18, 1984

[54] NITROSOUREA DERIVATIVES

[76] Inventor: Tetsuo Suami, 5-8, Nakamachi 3-chome, Musashino, Japan

[21] Appl. No.: 313,597

[22] Filed: Oct. 21, 1981

[30] Foreign Application Priority Data

Oct. 30, 1980 [JP] Japan ................. 55-151500

[51] Int. Cl.³ .............. A61K 37/00; A61K 31/70; C07C 103/52; C07H 15/20
[52] U.S. Cl. .............. 424/177; 260/112.5 R; 536/17.7; 424/180
[58] Field of Search ............. 536/17.7; 564/33; 260/112.5 R; 424/180, 177

[56] References Cited

U.S. PATENT DOCUMENTS

| | | | |
|---|---|---|---|
| 4,057,684 | 11/1977 | Kimura et al. | 536/17.7 |
| 4,180,655 | 12/1979 | Suami et al. | 564/33 |
| 4,182,757 | 1/1980 | Tsujihara et al. | 564/33 |
| 4,237,273 | 12/1980 | Horvath et al. | 564/33 |
| 4,367,239 | 1/1983 | Bregnedal et al. | 564/33 |

FOREIGN PATENT DOCUMENTS 2477142  4/1981  France ................. 564/33

Primary Examiner—Ethel G. Love
Attorney, Agent, or Firm—Larson and Taylor

[57] ABSTRACT

Novel nitrosourea derivatives are provided which possess a high level of inhibitory activity against leukemia and tumors and which are therefore useful for pharmaceutical purposes. The compounds have the structure represented by formula (I):

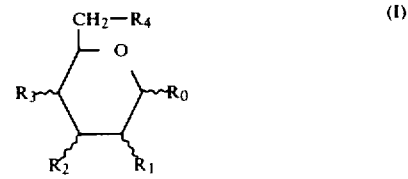

wherein $R_0$ represents —OH or —$OC_mH_{2m+1}$ where m is an integer of 1 to 3 and one of $R_1$, $R_2$, $R_3$ and $R_4$ represents

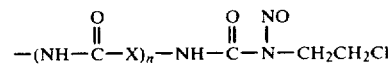

where X is

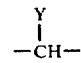

or an alkylene group of 1 to 3 carbon atoms, n is an integer of 1 to 3 and Y is the group on the α-carbon atom of an α-amino acid and each of the remaining three represents —OH; or wherein $R_0$ represents

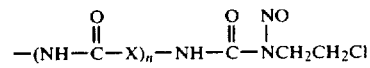

and $R_1$, $R_2$, $R_3$ and $R_4$ each represent —OH; or by formula (II):

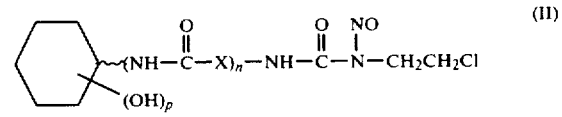

wherein X and n have the same meanings as above; and p is an integer of 1 to 5.

6 Claims, No Drawings

NITROSOUREA DERIVATIVES

BACKGROUND OF THE INVENTION

This invention relates to novel nitrosourea derivatives which exhibit a high level of inhibitory activity against leukemia and tumors, to a process for the preparation thereof and to their use for pharmaceutical purposes.

There are a variety of compounds which have been proposed as being effective for inhibiting leukemia and tumors, one class of which is nitrosourea derivatives. Among the nitrosourea derivatives, streptozotocin [N-(N'-methyl-N'-nitrosocarbamoyl)-D-glucosamine] and its derivatives such as methyl glucosaminides are typical ones early developed (refer to U.S. Pat. No. 3,577,406 and U.S. Pat. No. 3,767,640, for example), but they are not satisfactory yet because of insufficient activity against leukemia and tumors and/or of undesirable side effects thereof. Another class of nitrosourea derivatives is a series of glycosyl derivatives of nitrosoureas which I have recently proposed, among which the most interesting compound is 1-(2-chloroethyl)-3-($\beta$-D-glucopyranosyl)-1-nitrosourea (abbreviated as GANU) which has a broad spectrum of antitumor activity against a wide variety of experimental leukemia and tumors with positive expectation of the efficacy in human cancer chemotherapy (refer to T. Suami et al., U.S. Pat. No. 4,086,415, U.S. Pat. No. 4,157,439 and U.S. Pat. No. 4,220,643). A further class of nitrosourea derivatives I have already proposed is 1-(2-chloroethyl)-3-(mono- or poly-hydroxy-substituted cyclohexyl)-1-nitrosoureas, of which the most preferred one is 1-(2-chloroethyl)-3-(1,3/2N-dihydroxycyclohexyl)-1-nitrosourea (abbreviated as DONU) which also has a broad spectrum of antitumor activity against a wide variety of experimental leukemia and tumors with a very low toxicity (refer to T. Suami et al., U.S. Pat. No. 4,180,655).

BRIEF SUMMARY OF THE INVENTION

I have now found, as a result of my continuing investigations, a new series of nitrosourea derivatives which also possess a high inhibitory activity against leukemia and tumors with a low toxicity as corroborated by in vivo tests.

According to a first aspect of this invention, therefore, there are provided as new compounds nitrosourea derivatives of formula (I):

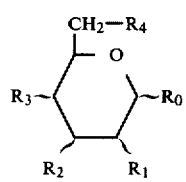

wherein $R_0$ represents —OH or —OC$_m$H$_{2m+1}$ where m is an integer of 1 to 3 and one of $R_1$, $R_2$, $R_3$ and $R_4$ represents

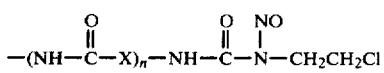

where X is

or an alkylene group of 1 to 3 carbon atoms, n is an integer of 1 to 3 and Y is the group on the α-carbon atom of an α-amino acid and each of the remaining three represents —OH; or wherein $R_0$ represents

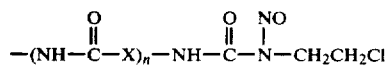

and $R_1$, $R_2$, $R_3$ and $R_4$ each represent —OH.

In formula (I), the monosaccharide skeleton may take the configuration of glucose, mannose, galactose, talose, idose, gulose, altrose or allose. In the definition of Y above, the words "the group on the α-carbon atom of an α-amino acid" mean a group which forms an α-amino acid when attached to a carbon atom to which an amino group, a carboxyl group and a hydrogen atom have been attached. Thus, the group

means such residual moiety of an α-amino acid that will occur or be derived when the α-amino group and the α-carboxyl group are removed from the molecule of the α-amino acid. For example, the group

may be of the formula:

which is derived from alanine by the removal of the amino and carboxyl groups from the alanine molecule, or of the formula:

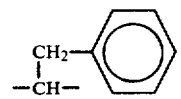

which is derived from phenylalanine similarly, or of the formula:

which is derived from serine, or of the formula:

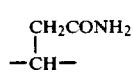

which is derived from asparagine, and so on. Typical examples of such residual group Y are those on the α-carbon atom of alanine, phenylalanine, serine, tryptophan, methionine, cysteine, tyrosine, valine, leucine, isoleucine, threonine, aspartic acid, asparagine, glutamic acid, glutamine, lysine, hydroxylysine, histidine and arginine and a di- or a polypeptide derived from any possible combination of α-amino acids.

I have further found that mono- and poly-hydroxy-substituted cyclohexyl homologues of nitrosourea derivatives of formula (I), which are also new compounds, exhibit similarly a high inhibitory activity against leukemia and tumors with a low toxicity as evidenced by in vivo tests.

According to another aspect of this invention, therefore, there are provided as new compounds nitrosourea derivatives of formula (II):

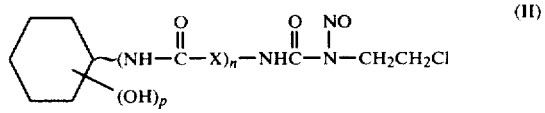

wherein X represents

or an alkylene group of 1 to 3 carbon atoms where Y is the group on the α-carbon atom of an α-amino acid; n is an integer of 1 to 3; and p is an integer of 1 to 5.

In the definition of Y above, the words "the group on the α-carbon atom of an α-amino acid" have the same meaning as given above with respect to formula (I).

The nitrosourea derivatives of formulae (I) and (II) according to this invention inherently have two, i.e. α and β, anomers. I have found that both the anomers and a mixture thereof exhibit a high inhibitory activity against leukemia and tumors.

DETAILED DESCRIPTION OF THE INVENTION

Typical examples of the nitrosourea derivatives of formula (I) may include:
methyl 2'-[N-[N-(2-chloroethyl)-N-nitroso-carbamoyl]-glycyl]amino-2'-deoxy-α-D-glucopyranoside;
methyl 2'-[N-[N-(2-chloroethyl)-N-nitroso-carbamoyl]-β-alanyl]amino-2'-deoxy-α-D-glucopyranoside;
methyl 2'-[N-[N-(2-chloroethyl)-N-nitroso-carbamoyl]amino-n-butyryl]amino-2'-deoxy-α-D-glucopyranoside;
methyl 2'-[N-[N-(2-chloroethyl)-N-nitroso-carbamoyl]-L-alanyl]amino-2'-deoxy-α-D-glucopyranoside;
methyl 3'-[N-[N-(2-chloroethyl)-N-nitroso-carbamoyl]-glycyl]amino-3'-deoxy-α-D-mannopyranoside;
methyl 3'-[N-[N-(2-chloroethyl)-N-nitroso-carbamoyl]-glycyl]-glycyl]amino-3'-deoxy-α-D-glucopyranoside;
methyl 2'p-[N-[N-(2-chloroethyl)-N-nitroso-carbamoyl]-L-seryl]amino-2'-deoxy-α-D-glucopyranoside;
1'-[N-[N-(2-chloroethyl)-N-nitroso-carbamoyl]-glycyl]amino-1'-deoxy-β-D-glucopyranose;
methyl 2'-[[N-[N-(2-chloroethyl)-N-nitroso-carbamoyl]-glycyl]-glycyl]amino-2'-deoxy-α-glucopyranoside;
methyl 2'-[N-[N-(2-chloroethyl)-N-nitroso-carbamoyl]-D-alanyl]amino-2'-deoxy-α-D-glucopyranoside;
2'-[N-[N-(2-chloroethyl)-N-nitroso-carbamoyl]-glycyl]amino-2'-deoxy-D-glucopyranose;
methyl 6'-N-[N-(2-chloroethyl)-N-nitroso-carbamoyl]-glycyl]amino-6'-deoxy-α-D-glucopyranoside;
1'-[N-[N-(2-chloroethyl)-N-nitroso-carbamoyl]-β-alanyl]amino-1'-deoxy-β-D-glucopyranose; and
1'-[N-[N-(2-chloroethyl)-N-nitroso-carbamoyl]amino-n-butyryl]amino-1'-deoxy-β-D-glucopyranose.

Typical examples of the nitrosourea derivatives of formula (II) may include:
(1'/2',6')-1'-[N-[N-(2-chloroethyl)-N-nitroso-carbamoyl]-glycyl]amino-2',6'-cyclohexanediol;
(1'/2',6')-1'-[N-[N-(2-chloroethyl)-N-nitroso-carbamoyl]amino-n-butyryl]amino-2',6'-cyclohexanediol;
(1'/2',6')-1'-[N-[N-(2-chloroethyl)-N-nitroso-carbamoyl]-β-alanyl]amino-2',6'-cyclohexanediol; and
(1'/2',6')-1'-[N-[N-(2-chloroethyl)-N-nitroso-carbamoyl]-asparaginyl]-amino-2',6'-cyclohexanediol.

Antileukemic activity of some typical nitrosourea derivatives of formulae (I) and (II) according to this invention was tested on Leukemia L 1210 in mice, details of which are given below.

| Compounds | |
|---|---|
| No. 1 | Methyl 2'-[N—[N—(2-chloroethyl)-N—nitroso-carbamoyl]-glycyl]amino-2'-deoxy-α-D-glucopyranoside [formula (I), $R_0 = \alpha\text{-OCH}_3$, $R_1 = \alpha\text{-NHCCH}_2\text{NHCNCH}_2\text{CH}_2\text{Cl}$, $R_2 = \beta\text{-OH}$, $\overset{\|}{O}$ $\overset{\|\|}{ONO}$ $R_3 = \alpha\text{-OH}, R_4 = \text{OH}]$ |
| No. 2 | Methyl 2'-[N—[N—(2-chloroethyl)-N—nitroso-carbamoyl]-β-alanyl]amino-2'-deoxy-α-D-glucopyranoside [formula (I), $R_0 = \alpha\text{-OCH}_3$, $R_1 = \alpha\text{-NHCCH}_2\text{CH}_2\text{NHCNCH}_2\text{CH}_2\text{Cl}$, $\overset{\|}{O}$ $\overset{\|\|}{ONO}$ $R_2 = \beta\text{-OH}, R_3 = \alpha\text{-OH}, R_4 = \text{OH}]$ |
| No. 3 | Methyl 2'-[N—[N—(2-chloroethyl)-N—nitroso-carbamoyl]amino-n-butyryl]amino-2'-deoxy-aα-D-glucopyranoside [formula (I), $R_0 = \alpha\text{-OCH}_3$, $R_1 = \alpha\text{-NHC(CH}_2)_3\text{NHCNCH}_2\text{CH}_2\text{Cl}$ $\overset{\|}{O}$ $\overset{\|\|}{ONO}$ $R_2 = \beta\text{-OH}, R_3 = \alpha\text{-OH}, R_4 = \text{OH}]$ |
| No. 4 | Methyl 2'-[N—[N—(2-chloroethyl)-N—nitroso-carbamoyl]-L-alanyl]amino-2'-deoxy-α-D-glucopyranoside |

-continued

| Compounds | |
|---|---|

[formula (I), $R_0 = \alpha\text{-}OCH_3$, $R_1 = \alpha\text{-}NHCCH\text{—}CH_3$
$\phantom{xxxxxxxxxxxxxxxxxxxxxxxxxxxxxxx}\underset{O}{\overset{\|}{}}\underset{\phantom{x}}{\underset{ONO}{\overset{\|\,\|}{NHCNCH_2CH_2Cl,}}}$ $R_2 = \beta\text{-}OH$, $R_3 = \alpha\text{-}OH$, $R_4$ 32 OH]

No. 5  Methyl 2'-[N—[N—(2-chloroethyl)-N—nitroso-carbamoyl]-D-alanyl]amino-2'-deoxy-α-D-glucopyranoside
[formula (I), $R_0 = \alpha\text{-}OCH_3$, $R_1 = \alpha\text{-}NHCCHCH_3$
$\phantom{xxxxxxxxxxxxxxxxxxxxxxxxxxxxxxx}\overset{\|}{O}\phantom{x}\underset{ONO}{\overset{\|\,\|}{NHCNCH_2CH_2Cl,}}$ $R_2 = \beta\text{-}OH$, $R_3 = \alpha\text{-}OH$, $R_4 = OH$]

No. 6  1'-[N—[N—(2-Chloroethyl)-N—nitroso-carbamoyl]-glycyl]amino-1'-deoxy-β-D-glucopyranose [formula
(I), $R_0 = \beta\text{-}NHCCH_2NHCNCH_2CH_2Cl$, $R_1 = \alpha\text{-}OH$, $R_2 = \beta\text{-}OH$,
$\phantom{xxxxxxxxxx}\overset{\|}{O}\phantom{xxxxxx}\overset{\|\,\|}{ONO}$ $R_3 = \alpha\text{-}OH$, $R_4 = OH$]

No. 7  2'-[N—[N—(2-Chloroethyl)-N—nitroso-carbamoyl]-glycyl]amino-2'-deoxy-D-glucopyranose [formula
(I), $R_0 = OH$, $R_1 = \alpha\text{-}NHCCH_2NHCNCH_2CH_2Cl$, $R_2 = \beta\text{-}OH$,
$\phantom{xxxxxxxxxxxxxxxx}\overset{\|}{O}\phantom{xxxxxx}\overset{\|\,\|}{ONO}$ $R_3 = \alpha\text{-}OH$, $R_4 = OH$]

No. 8  Methyl 6'-[N—[N—(2-chloroethyl)-N—nitroso-carbamoyl]-glycyl]amino-6'deoxy-α-D-glucopyranoside [formula
(I), $R_0 = \alpha\text{-}OCH_3$, $R_1 = \alpha\text{-}OH$, $R_2 = \beta\text{-}OH$, $R_3 = \alpha\text{-}OH$, $R_4 = $
—NHCCH_2NHCNCH_2CH_2Cl]
$\phantom{xx}\overset{\|}{O}\phantom{xxxxx}\overset{\|\,\|}{ONO}$ No. 9  1'-[N—[N—(2-Chloroethyl)-N—nitroso-carbamoyl]-β-alanyl]amine-1'-deoxy-β-D-glucopyranose [formula
(I), $R_0 = \beta\text{-}NHC(CH_2)_2NHCNCH_2CH_2Cl$, $R_1 = \alpha\text{-}OH$, $R_2 = \beta\text{-}OH$,
$\phantom{xxxxxxxxxxx}\overset{\|}{O}\phantom{xxxxxxx}\overset{\|\,\|}{ONO}$ $R_3 = \alpha\text{-}OH$, $R_4 = OH$]

No. 10  1'-[N—[N—(2-Chloroethyl)-N—nitroso-carbamoyl]-amino-n-butyryl]amino-1'-deoxy-β-D-glucopyranose
[formula (I), $R_0 = \beta\text{-}NHC(CH_2)_3NHCNCH_2CH_2Cl$, $R_1 = \alpha\text{-}OH$,
$\phantom{xxxxxxxxxxxxxxx}\overset{\|}{O}\phantom{xxxxxxx}\overset{\|\,\|}{ONO}$ $R_2 = \beta\text{-}OH$, $R_3 = \alpha\text{-}OH$, $R_4 = OH$]

No. 11  (1'/2',6')-1'-[N—[N—(2-Chloroethyl)-N—nitroso-carbamoyl]-glycyl]amino-2',6'-cyclohexanediol
[formula (II), 1' $= \beta\text{-}NHCCH_2NHCNCH_2CH_2Cl$, 2' and
$\phantom{xxxxxxxxxxxxxxx}\overset{\|}{O}\phantom{xxxxxx}\overset{\|\,\|}{ONO}$ 6' $= \alpha\text{-}OH$]

No. 12  (1'/2',6')-1'-[N—[N—(2-Chloroethyl)-N—nitroso-carbamoyl]-asparaginyl]amino-2',6'-cyclohexanediol
[formula (II), 1' $= \beta\text{-}NHCCHCH_2CONH_2$
$\phantom{xxxxxxxxxxxxxxxxxxxxxxx}\overset{\|}{O}\underset{\phantom{x}}{\underset{ONO}{\overset{\|\,\|}{NHCNCH_2CH_2Cl,}}}$ 2' and 6' $= \alpha\text{-}OH$]

No. 13  (1'/2', 6')-1'-[N—[N—(2-Chloroethyl)-N—nitroso-carbamoyl]-amino-n-butyryl]amino-2',6'-cyclohexanediol
[formula (II), 1' $= \beta\text{-}NHC(CH_2)_3NHCNCH_2CH_2Cl$,
$\phantom{xxxxxxxxxxxxx}\overset{\|}{O}\phantom{xxxxxx}\overset{\|\,\|}{ONO}$ 2' and 6' $= \alpha\text{-}OH$]

No. 14  (1'/2',6')-1'-[N—[N—(2-chloroethyl)-N—nitroso-carbamoyl]-β-alanyl]amino-2',6'-cyclohexanediol
[formula (II), 1' $= \beta\text{-}NHC(CH_2)_2NHCNCH_2CH_2Cl$,
$\phantom{xxxxxxxxxxxxx}\overset{\|}{O}\phantom{xxxxxx}\overset{\|\,\|}{ONO}$ 2' and 6' $= \alpha\text{-}OH$]

Animals

Male BDF$_1$ mice, aged about 7 weeks old and weighing 22±1 g were used in groups of five animals for each test.

Tumor cells

Leukemia L 1210 cells were inoculated intraperitoneally in a concentration of $1 \times 10^6$ cells/0.05 ml/mouse.

Method

The test compound was dissolved in a physiological salt solution to give a series of solutions in predetermined concentrations and 0.1 ml of the each solution was administered intraperitoneally to each mouse once a day from the 24th hour after the tumor cell inoculation for 3 consecutive days. The antileukemic activity of the test compound was assessed by mean survival days, percentage increase in life-span and the volume of ascites. The percentage increase in life-span (ILS) was calculated as follows:

$$ILS\ (\%) = \frac{T - C}{C} \times 100$$

T: The mean survival days of the treated animals
C: The mean survival days of the untreated animals The control test for this purpose was carried out in the same way as that used for each test compound except that 0.1 ml of the physiological salt solution was administered in place of the solution of the test compound.

The test results are shown in the following table.

| Compound No. | Dose (mg/kg) | Mean survival days Treated/Control | ILS (%) | Volume of ascites (ml) Treated/Control |
|---|---|---|---|---|
| 1 | 32 | >39.0/7.0 | >457.1 | 0/0.7 |
|   | 16 | >28.2/7.0 | >302.9 | 0.3/0.7 |
|   | 8  | 13.6/7.0 | 94.3 | 0.3/0.7 |
|   | 4  | 9.6/7.0 | 37.1 | 0.2/0.7 |
|   | 2  | 10.0/7.0 | 42.9 | 0.2/0.7 |
|   | 1  | 9.2/7.0 | 31.4 | 0.3/0.7 |
|   | 0.5 | 7.6/7.0 | 8.6 | 0.2/0.7 |
| 2 | 32 | 17.8/7.0 | 154.3 | 0/0.7 |
|   | 8 | 11.7/7.0 | 67.1 | 0.9/0.7 |
|   | 2 | 8.6/7.0 | 22.9 | 0.1/0.7 |
|   | 0.5 | 7.0/7.0 | 0 | 0.3/0.7 |
| 3 | 32 | 17.3/7.0 | 147.1 | 0.3/0.7 |
|   | 8 | 10.8/7.0 | 54.3 | 0.9/0.7 |
|   | 2 | 7.8/7.0 | 11.4 | 0/0.7 |
|   | 0.5 | 7.2/7.0 | 2.9 | 0.6/0.7 |
| 4 | 32 | >24.3/7.0 | >247.1 | 0.9/0.7 |
|   | 8 | 13.5/7.0 | 92.9 | 1.0/0.7 |
|   | 2 | 9.4/7.0 | 34.3 | 0/0.7 |
|   | 0.5 | 7.2/7.0 | 2.9 | 0.4/0.7 |
| 5 | 48 | 12.6/7.6 | 65.8 | 0/0.6 |
|   | 32 | >50.8/7.6 | >568.4 | 0/0.6 |
|   | 8 | >42.8/7.6 | >463.2 | 0.2/0.6 |
|   | 2 | 14.4/7.6 | 89.5 | 1.0/0.6 |
|   | 0.5 | 9.8/7.6 | 28.9 | 0.8/0.6 |
| 6 | 24 | >26.2/7.0 | >274.3 | 0.1/0.6 |
|   | 16 | 15.6/7.0 | 122.9 | 0.5/0.6 |
|   | 4 | 10.0/7.0 | 42.9 | 0.3/0.6 |
| 7 | 96 | 10.0/7.6 | 31.6 | 0/0.6 |
|   | 64 | >43.4/7.6 | >471.0 | 0/0.6 |
|   | 48 | >26.2/7.6 | >244.7 | 0.6/0.6 |
|   | 32 | 15.2/7.6 | 100.0 | 1.0/0.6 |
|   | 8 | 8.8/7.6 | 15.8 | 0.8/0.6 |
|   | 2 | 7.8/7.6 | 2.6 | 0.4/0.6 |
|   | 0.5 | 7.4/7.6 | −2.6 | 0.7/0.6 |
| 8 | 48 | >18.7/7.2 | >159.7 | 0/0.6 |
|   | 32 | >50.8/7.2 | >605.6 | 0/0.6 |
|   | 8 | 15.0/7.2 | 108.3 | 0.9/0.6 |
|   | 2 | 9.8/7.2 | 36.1 | 0.2/0.6 |
|   | 0.5 | 8.0/7.2 | 11.1 | 0.3/0.6 |
| 9 | 48 | >29.7/7.0 | >324.3 | 0/0.8 |
|   | 32 | >51.0/7.0 | >628.6 | 0/0.8 |
|   | 8 | 11.0/7.0 | 57.1 | 0.7/0.8 |
|   | 2 | 9.6/7.0 | 37.1 | 0.1/0.8 |
|   | 0.5 | 7.4/7.0 | 5.7 | 0.6/0.8 |
| 10 | 32 | >25.6/7.0 | >265.7 | 0/0.8 |
|    | 8 | 11.8/7.0 | 68.6 | 0.4/0.8 |
|    | 2 | 9.0/7.0 | 28.6 | 0.3/0.8 |
|    | 0.5 | 7.0/7.0 | 0 | 0.8/0.8 |
| 11 | 24 | >60.0/7.0 | >757.1 | 0/0.6 |
|    | 16 | >36.0/7.0 | >414.3 | 0/0.6 |
| 12 | 32 | 9.0/7.0 | 28.6 | 0/1.1 |
|    | 16 | 18.8/7.0 | 168.6 | 1.1/1.1 |
|    | 8 | 14.0/7.0 | 100.0 | 0.7/1.1 |
|    | 2 | 9.4/7.0 | 34.3 | 0.1/1.1 |
|    | 0.5 | 7.8/7.0 | 11.4 | 0.7/1.1 |
| 13 | 48 | >45.4/7.7 | >489.6 | 0/0.8 |
|    | 32 | >33.4/7.7 | >345.3 | 0/0.8 |
|    | 8 | 12.8/7.7 | 66.2 | 0.6/0.8 |
|    | 2 | 10.0/7.7 | 29.9 | 0/0.8 |
|    | 0.5 | 8.0/7.7 | 2.6 | 0.7/0.8 |
| 14 | 48 | >60.0/7.6 | >689.5 | 0/0.6 |
|    | 32 | >60.0/7.6 | >689.5 | 0/0.6 |
|    | 8 | 15.2/7.6 | 100.0 | 0.8/0.6 |
|    | 2 | 10.6/7.6 | 39.5 | 0.4/0.6 |
|    | 0.5 | 8.2/7.6 | 7.9 | 0.1/0.6 |

It will be clearly appreciated from the above test results that the novel nitrosourea derivatives of formulae (I) and (II) according to this invention show a high value of ILS in a very low dose and are therefore expected to be useful in human chemotherapy of leukemic and tumor diseases.

The nitrosourea derivatives of formulae (I) and (II) according to this invention are further characterized by their low toxicity. Thus, acute toxicity represented by LD$_{50}$ of some typical compounds of formulae (I) and (II), when administered intraperitoneally to BDF$_1$ male mice aged about 5-weeks old and observed after the lapse of 21 days, is within the range of 50 to 150 mg/kg.

According to a further aspect of this invention, therefore, there is provided a pharmaceutical composition comprising a therapeutically effective amount of a nitrosourea derivative of formula (I) or (II) in association with a pharmaceutically acceptable excipient, carrier or diluent.

The pharmaceutical composition may be in a form known per se to suit the route of administration that is oral or injection administration for man or oral, injection or intraperitoneal administration for animals. In general, therefore, the pharmaceutical composition may take such form as an ampoule, capsule, tablet, powder, granule and the like to adapt it for oral or injection administration.

This invention also includes as a further aspect thereof a method for the therapeutic treatment of leukemia and tumor diseases in man and animals which comprises administering to the patient a therapeutically effective amount, at suitable intervals, of a nitrosourea derivative of formula (I) or (II) above. It will be appreciated that the amount of the nitrosourea derivative to be actually applied will vary dependent upon the particular compound used, the particular composition formulated, the mode of application, the route of administration and other variables. Many factors which modify the action of the drug will be taken into account by those skilled in the art, for example, age, body weight, sex, diet, time of administration, route of administration, rate of metabolism or excretion, drug combination, sensitivity, and severity or condition of the disease. Optimal application dose for a given set of conditions can be ascertained by those skilled in the art using conventional tests for the dosage determination in view of the above guidelines.

According to a still further aspect of this invention, there is provided a process for the preparation of nitrosourea derivatives of formulae (I) and (II) above which comprises reacting a compound of either formula (III) or formula (IV):

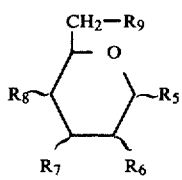

wherein $R_5$ represents —OH or —OC$_m$H$_{2m+1}$ where m is an integer of 1 to 3 and one of $R_6$, $R_7$, $R_8$ and $R_9$ represents

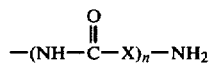

where X is

or an alkylene group of 1–3 carbon atoms, n is an integer of 1 to 3 and Y is the group on the α-carbon atom of an α-amino acid and each of the remaining three represents —OH; or wherein $R_5$ represents

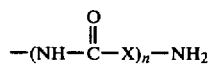

and $R_6$, $R_7$, $R_8$ and $R_9$ each represent —OH;

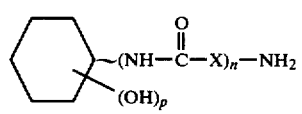

wherein X and n have the same meanings as defined above and p is an integer of 1 to 5; with p-nitrophenyl N-(2-chloroethyl)-N-nitroso-carbamate.

The process according to this invention relates to a peptidation reaction between the compound of formula (III) or (IV) and p-nitrophenyl N-(2-chloroethyl)-N-nitroso-carbamate and is usually carried out in a solvent, e.g. tetrahydrofuran, in the presence of a base, e.g. triethylamine, at a temperature of 0° C.–50° C. The compound of formula (I) or (II) thus formed may be isolated easily from the reaction solution and purified by a known purification technique such as a treatment with an ion-exchange resin and a column chromatography.

The starting compound of formula (III) or (IV) may be prepared through a reaction of a monoamino-substituted glycose or a monoamino-substituted mono- or poly-hydroxy-cyclohexane with an N-protected α-amino acid in a known manner.

The following is one typical example of the process through which a nitrosourea derivative of formula (I) may be prepared from methyl D-glycosaminide of formula (V).

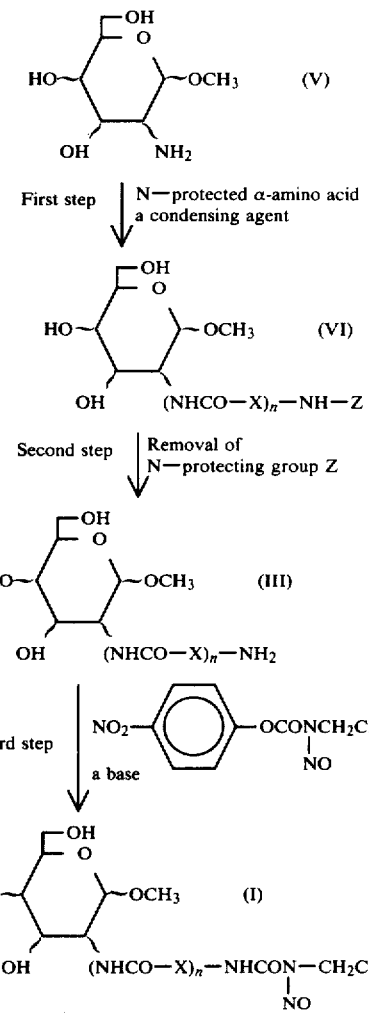

The first step is a peptidation reaction between a methyl D-glycosaminide, e.g. methyl D-glucosaminide, and an N-protected α-amino acid. The N-protected α-amino acid may preferably be used in the form of an active ester which is prepared by reacting the N-protected α-amino acid with N-hydroxysuccinimide and dicyclohexylcarbodiimide in a suitable solvent at a relatively low temperature, preferably under ice-cooling. The reaction of the starting compound of formula (V) (methyl D-glycosaminide) with said active ester may be effected in a suitable solvent such as dimethylformamide, methanol and ethanol, in the presence of a base such as triethylamine, N,N-dimethylamine and monoethylamine, at a temperature of 0° C.–50° C.

The second step is a deprotection reaction for amino group and may be carried out by any conventional method. For the removal of a benzyloxycarbonyl group as an amino-protecting group, a catalytic hydrogenation in the presence of e.g. palladium-black catalyst is preferred.

The starting compound of formula (III) wherein 1-, 3-, 4- or 6-hydroxyl group was substituted by a group —(NHCO—X)$_n$—NH$_2$ may be prepared in the same manner as that explained above.

The following Examples illustrate the preparation of the nitrosourea derivatives of this invention together with the preparation of the starting and intermediate compounds.

EXAMPLE 1

(1) Preparation of p-nitrophenyl N-(2-chloroethyl)-carbamate

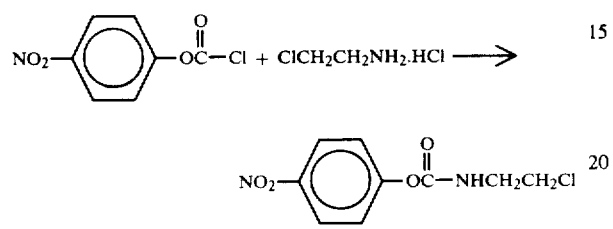

2-Chloroethylamine hydrochloride (2.0 g, 17.24 mmol.) was dissolved in water (2 ml) and to the solution was added sodium hydrogen carbonate (3.62 g, 43.09 mmol.) which had been substantially dissolved in water (25 ml), where the sodium hydrogen carbonate was completely dissolved with bubbling.

The resulting solution was added dropwise over 15 minutes to a solution of p-nitrophenylchloroformate (3.65 g, 18.11 mmol.) in acetone (50 ml) under ice-cooling and stirring and after continuing the stirring for further 5 minutes, water (80 ml) was added to the mixture, upon which crystals were deposited immediately. After the stirring was continued for further 10 minutes, the crystals were suction-filtered, washed with water and dried in vacuo. The crude crystals thus obtained were washed with a mixture of benzene and cyclohexane (1:1 by volume) and dried in vacuo to yield the titled compound (1.8 g).

Yield: 42.7%; m.p. 97°–98° C. (95° C. in literature).

Elemental analysis: Calculated for C$_9$H$_9$N$_2$O$_4$Cl, MW=244.635: C 44.18, H 3.71, N 11.45, Cl 14.49%; Found: C 44.34, H 3.76, N 11.34, Cl 14.73%.

(2) Preparation of p-nitrophenyl N-(2-chloroethyl)-N-nitroso-carbamate

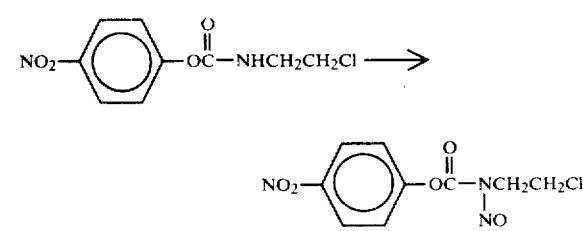

The compound obtained in (1) above (2.0 g, 8.18 mmol.) was dissolved in conc. nitric acid (sp. gr. 1.38) (30 ml) at room temperature. Sodium nitrate (900 mg, 13.0 mmol.) was added in small portions to the solution at 5°–10° C. under stirring. The addition of the sodium nitrite was carried out regularly regardless of the deposition of crystals which occurred upon cooling. After the completion of the addition of sodium nitrite, the mixture was further stirred under ice-cooling for one hour. Ice water (40 ml) was then added to the reaction mixture and the crystals formed were filtered, washed with a large amount of water and dried in vacuo. The residue was steeped in ethanol and heated at about 40° C., stored in a refrigerator overnight, filtered and washed with ethanol to give the titled compound (2.08 g).

Yield: 92.7%; m.p. 117°–118° C. (116° C. in literature). Elemental analysis: Calculated for C$_9$H$_8$N$_3$O$_5$Cl, MW=273.635: C 39.50, H 2.95, N 15.36, Cl 12.96%; Found: C 39.73, H 3.15, N 15.39, Cl 13.13%.

EXAMPLE 2

Preparation of methyl α-D-glucosaminide

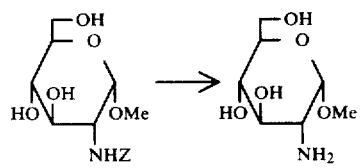

Z: benzyloxycarbonyl.

Methyl N-benzyloxycarbonyl-α-D-glucosaminide (1.0 g) which was prepared according to Neuberger et al.'s process [see A. Neuberger and R. T. Rivens, J. Chem. Soc., 122 (1939)] was dissolved in ethanol (15 ml) and the solution was subjected to catalytic hydrogenation in the presence of Pd-black (100 mg) as catalyst under the initial hydrogen pressure of 50 psi for 6 hours. After the removal of the catalyst by spontaneous filtration, the reaction solution was concentrated in vacuo and dried in vacuo to obtain the titled compound as oily residue in a quantitative yield. The product was used as such in the next reaction step.

EXAMPLE 3

Preparation of an active ester of N-carbobenzoxyglycine

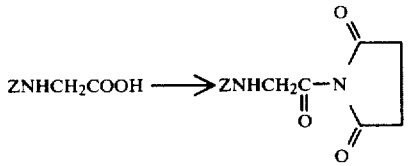

N-Carbobenzoxyglycine (a commercial product) (2.0 g, 9.56 mmol.) and N-hydroxysuccinimide (1.12 g, 9.75 mmol.; 1.02 moles per mole of the first reagent) were dissolved in dioxane (20 ml) and dicyclohexylcarbodiimide (hereinafter referred to as DCC) (2.01 g, 9.75 mmol.; 1.02 moles per mole of the first reagent) was added to the solution under ice-cooling and stirring. The stirring was continued for further one hour under the same conditions and stored in a refrigerator overnight.

The reaction mixture was filtered to remove urea deposited and the filtrate was concentrated in vacuo to obtain an oily residue. The residue was dissolved in chloroform and ethylether was added to the solution in an amount not to make the solution turbid. The solution was stored in a refrigerator, when the active ester crystallized out. After washing with ethylether, the titled compound (2.32 g) was obtained.

Yield: 83.6%; m.p. 112°–113° C. (113°–114° C. in literature).

EXAMPLE 4

Preparation of methyl 3-amino-α-D-mannopyranoside hydrochloride

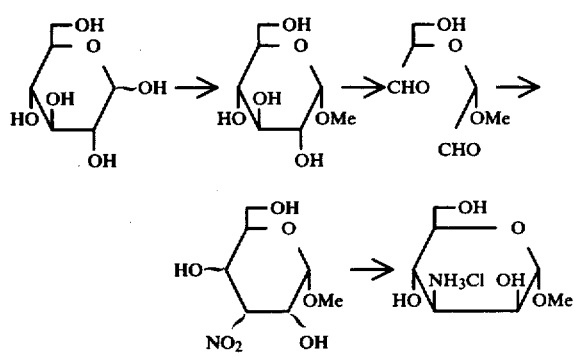

The titled compound was synthesized through the above route in accordance with the process proposed by A. C. Richardson [J. Chem. Soc., 373 (1962)].

m.p. 212°–215° C. (with decomposition and coloration).

Specific rotation $[\alpha]_D^{20} = +52.6°$ (c 0.4, H$_2$O).

Elemental analysis: Found: C 36.63, H 6.82, N 6.02%; Calculated for C$_7$H$_{16}$NO$_5$Cl, MW=229.647: C 36.61, H 7.02, N 6.10%.

EXAMPLE 5

(1) Preparation of methyl 4,6-O-benzylidene-3-deoxy-3-phenylazo-α-D-glucopyranoside

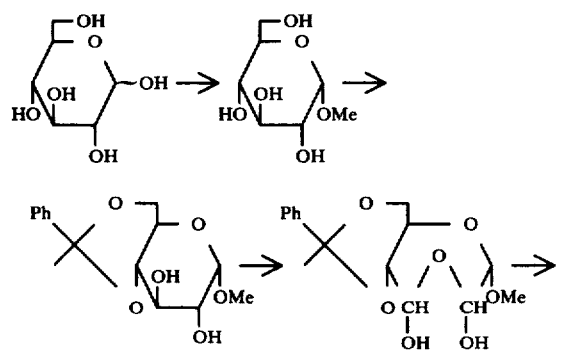

The titled compound was prepared through the above route in accordance with the process proposed by R. D. Guthrie and G. J. F. Chittenden [J. Chem. Soc., 3658–3665 (1963)].

m.p. 187.5°–188° C. (182°–183° C. in literature).

$[\alpha]_D^{23} + 9.8$ (c 0.94, chloroform) [$[\alpha]_D^{20} + 8.6$ (c 1.81, chloroform) in literature].

Elemental analysis: Found: C 64.96, H 6.01, N 7.61%; Calculated for C$_{20}$H$_{22}$N$_2$O$_5$, MW=370.392: C 64.85, H 5.99, N 7.56%.

(2) Preparation of methyl 4,6-O-benzylidene-3-(benzyloxycarbonyl)amino-3-deoxy-α-D-glucopyranoside

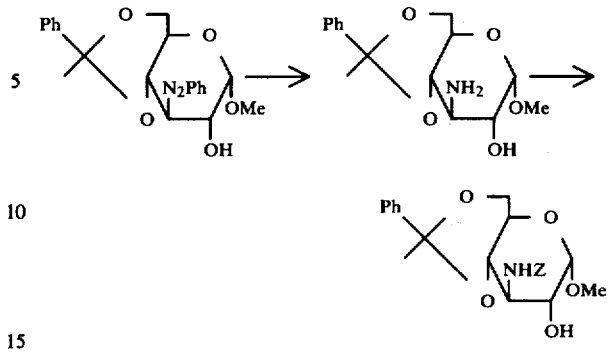

The compound prepared in (1) above (1.0 g, 2.70 mmol.) was dissolved in methanol (10 ml) under heating and glacial acetic acid (2 drops) was added thereto. The solution was subjected to catalytic hydrogenation in the presence of Raney nickel T-4 catalyst (1 spatula) at 50° C. under the initial hydrogen pressure of 45 psi for 21 hours. TLC of the reaction mixture with a developer system of 5:1 (by volume) benzene-ethyl acetate gave a single spot at the origin which was positive to ninhydrin reaction, after which the catalyst was removed by spontaneous filtration and the filtrate was concentrated in vacuo to a volume of about 10 ml.

To the concentrate was added an aqueous solution of sodium hydrogen carbonate (600 mg, 2 moles per mole of the starting compound) in water (8 ml) and then added dropwise a 30% solution of benzyloxycarbonyl chloride in toluene (2.73 ml, 1.5 moles per mole of the starting compound) at room temperature under a strong stirring. Immediately, there occurred deposition of solid matters, but the stirring was continued for further 30 minutes before filtration. The filter cake was washed well with water and dried in vacuo, affording crude crystals of the titled compound which was recrystallized from chloroform to yield needle crystals (365 mg).

Yield: 86.0%; m.p. 252°–254° C.

Elemental analysis: Found: C 63.35, H 5.91, N 3.44%; Calculated for C$_{22}$H$_{25}$NO$_7$, MW=415.428: C 63.60, H 6.07, N 3.37%.

EXAMPLE 6

(1) Preparation of methyl 2-[(benzyloxycarbonyl)-glycyl]amino-2-deoxy-α-D-glucopyranoside (A-1)

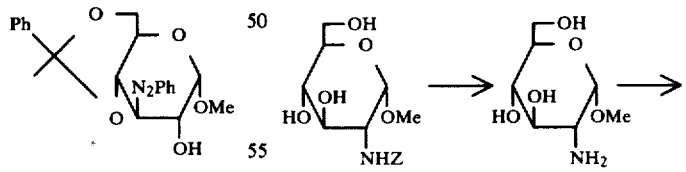

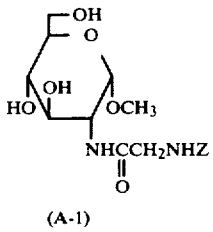

(A-1)

Methyl N-benzyloxycarbonyl-α-D-glucosaminide (1.82 g, 5.56 mmol) was treated in the same manner as that used in Example 2 to remove the benzyloxycarbonyl group, yielding methyl α-D-glucosaminide as an oily residue in a quantitative yield.

The oily residue was dissolved in dimethylformamide (5 ml) and triethylamine (1.54 ml, 2 moles per mole of the starting compound) was added to the solution. To the solution was added dropwise a solution of N-hydroxysuccinimide active ester of N-carbobenzoxy-glycine in dioxane (5 ml) under stirring and ice-cooling. After the completion of this addition, the reaction was continued for further one hour under the same conditions as above and then for 2 hours at room temperature. TLC of the reaction mixture with a developer system of 4:1 (by volume) chloroform-methanol gave a substantially single spot at $R_f$ 0.44 with a trace spot at the origin. The reaction solution was concentrated in vacuo to leave a white solid residue which was then washed with acetone and recrystallized from isopropyl alcohol affording the compound (A-1) as crystals (1.625 g).

Yield: 76.0%; m.p. 195°–195.5° C.; $[\alpha]_D^{23} = +87.2°$ (c 1, methanol).

Elemental analysis: Calculated for $C_{17}H_{24}N_2O_8$, MW=384.378: C 53.12, H 6.29, N 7.29%; Found: C 53.37, H 6.52, N 7.18%.

(2) Preparation of methyl 2'-[N-[N-(2-chloroethyl)-N-nitroso-carbamoyl]-glycyl]amino-2'-deoxy-α-D-glucopyranoside (AN-1).

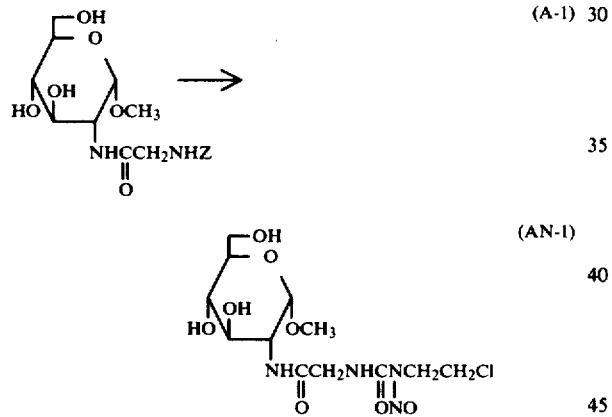

The compound (A-1) (220 mg, 0.572 mmol.) was dissolved in methanol (20 ml). The solution was hydrogenated in the presence of Pd-black (30 mg) as catalyst under the initial hydrogen pressure of 50 psi for 26 hours to remove the benzyloxycarbonyl group. The completion of reaction was confirmed by TLC, after which the catalyst was spontaneously filtered off and the filtrate was concentrated to a volume of about 5 ml with a partial crystallization. To the concentrate triethylamine (29 mg, 0.5 moles per mole of the starting compound) was added and then added dropwise over 15 minutes a solution of p-nitrophenyl N-(2-chloroethyl)-N-nitroso-carbamate (313 mg, 2 moles per mole of the starting compound) in tetrahydrofuran (hereinafter referred to as THF; 5 ml) under light-shielding. The reaction was continued for further 2 hours at room temperature under stirring. Then, TLC of the reaction mixture with a developer system of 4:1 (by volume) chloroform-methanol gave a main spot at Rf 0.40 for the main product showing a UV absorption and a secondary spot at Rf 0.18 for a small amount of a by-product showing no UV absorption and having unknown structure, but no spot at the origin. The reaction solution was concentrated in vacuo at room temperature to leave a deep yellow oily residue.

The residue was dissolved in a minimum amount of methanol required, to which isopropylether was added to precipitate an oil. The whole was stored in a refrigerator overnight, after which the supernatant liquid was removed and the oil was washed with isopropylether several times and dissolved in isopropyl alcohol. The solution was concentrated in vacuo to deposit a solid matter which was recovered by filtration, washed well with THF and then with a small amount of isopropyl alcohol to yield the compound (AN-1) (138 mg) which was confirmed as a single spot in TLC.

Yield: 62.7%; m.p. 163°–165° C. (with bubbling).
$[\alpha]_D^{23} = +93.1°$ (c 0.6, methanol).

Elemental analysis: Calculated for $C_{12}H_{21}N_4O_8Cl$, MW=384.777: C 37.46, H 5.50, N 14.56, Cl 9.21%; Found: C 37.38, H 5.39, N 14.84, Cl 9.04%.

EXAMPLE 7

(1) Preparation of methyl 2-[(benzyloxycarbonyl)-β-alanyl]amino-2-deoxy-α-D-glucopyranoside (A-2)

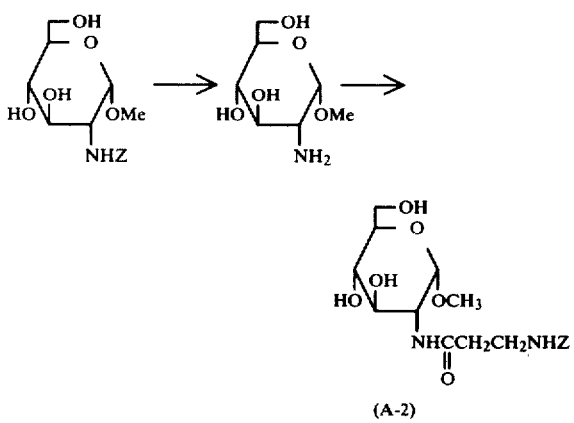

Methyl N-benzyloxycarbonyl-α-D-glucosaminide (1.466 g, 4.48 mmol.) was treated for the debenzyloxycarbonylation in the same manner as that used in Example 2, affording methyl α-D-glucosaminide as an oily residue in a quantitative yield.

N-Carbobenzoxy-β-alamine (1.00 g, 4.48 mmol.) (a commercial product available from Tokyo Kasei K.K.) and N-hydroxysuccinimide (516 mg, 4.48 mmol.) were dissolved in dioxane (5 ml). DCC (924 mg, 4.48 mmol.) was added to the solution under ice-cooling and stirring and the mixture was held at room temperature for 2 hours to proceed the reaction for the formation of the desired active ester.

The first-mentioned product, methyl α-D-glucosaminide in the form of an oily residue, was dissolved in anhydrous dimethylformamide (hereinafter referred to as DMF) (5 ml) and triethylamine (1.24 ml, 2 moles per mole of the starting compound). To the mixture was added dropwise under ice-cooling and stirring the second-mentioned product, the active ester of N-carbobenzoxy-β-alanine which had been filtered to remove dicyclohexylurea deposited. The reaction mixture was held under the same conditions as above for further one hour and then at room temperature for 2 hours to complete the reaction. TLC of the resultant reaction mixture with a developer system of 4:1 (by volume) chloroform-methanol showed a substantially single spot at $R_f$ 0.60 with a trace spot at the origin. The reaction solution was concentrated in vacuo to leave a yellow oily residue which was purified by a silica gel-column chromatography (silica gel: 100 g of Wako gel C-300, a product of Wako Junyaku K.K.; eluent: chloroform-methanol=9:1 by volume). The fractions corresponding to the compound (A-2) were collected and concentrated in vacuo to leave white crystals. Recrystallization from isopropyl alcohol followed by washing with acetone afforded the compound (A-2) as fine needle-like crystals (1.244 g).

Yield: 69.7%; m.p. 181.5°–182.5° C.; $[\alpha]_D^{23} = +86.4°$ (c 0.5, methanol).

Elemental analysis: Calculated for $C_{18}H_{26}N_2O_8$, MW=398.404: C 54.26; H 6.58; N 7.03%; Found: C 54.27; H 6.60; N 6.87%.

(2) Preparation of methyl 2'-[N-[N-(2-chloroethyl)-N-nitroso-carbamoyl]-β-alanyl]amino-2'-deoxy-α-D-glucopyranoside (AN-2)

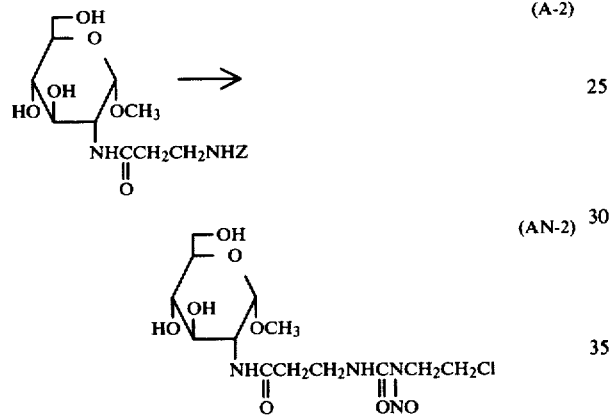

Compound (A-2) (200 mg, 0.502 mmol.) was dissolved in methanol (10 ml) and the solution was hydrogenated in the presence of Pd-black (30 mg) as catalyst under the initial hydrogen pressure of 50 psi for 6 hours to remove the benzyloxycarbonyl group. After the completion of reaction was confirmed by TLC, the catalyst was removed by spontaneous filtration and the filtrate was concentrated to a volume of about 5 ml with a partial crystallization. To the concentrate was added triethylamine (25 mg, 0.5 moles per mole of the starting compound) and then added dropwise over 15 minutes a solution of p-nitrophenyl N-(2-chloroethyl)-N-nitroso-carbamate (275 mg, 2 moles per mole of the starting material) in THF (5 ml) under light-shielding. The reaction was continued for further 2 hours at room temperature under stirring, after which TLC of the reaction solution with a developer system of 4:1 (by volume) chloroform-methanol showed a single spot at $R_f$ 0.42 for the desired product having a UV absorption and no spot at the origin. The reaction solution was concentrated in vacuo at room temperature to leave a deep yellow oil which was then dissolved in a minimum amount of acetone required. An amount of ethylether was added to the acetone solution to precipitate an oil. After the removal of the supernatant liquid, the oil was dissolved in a minimum amount of isopropyl alcohol required, to which an amount of isopropylether was added to precipitate an oil. Again, after the removal of the supernatant liquid, the oil was dissolved in isopropyl alcohol and the solution was concentrated sufficiently to deposit a solid mass, which was filtered and washed with isopropyl alcohol to yield the compound (AN-2) (143 mg) which was confirmed as a single spot in TLC.

Yield: 71.4%; m.p. 98°~100° C. (with bubbling).
$[\alpha]_D^{23} + 79.4°$ (c 0.64, methanol).

Elemental analysis: Calculated for $C_{13}H_{23}N_4O_8Cl$, MW=398.803: C 39.15, H 5.81, N 14.05, Cl 8.89%; Found: C 38.83, H 5.82, N 14.07, Cl 8.52%.

EXAMPLE 8

Preparation of methyl 2-[4'-(benzyloxycarbonyl)amino-n-butyryl]amino-2-deoxy-α-D-glucopyranoside (A-3)

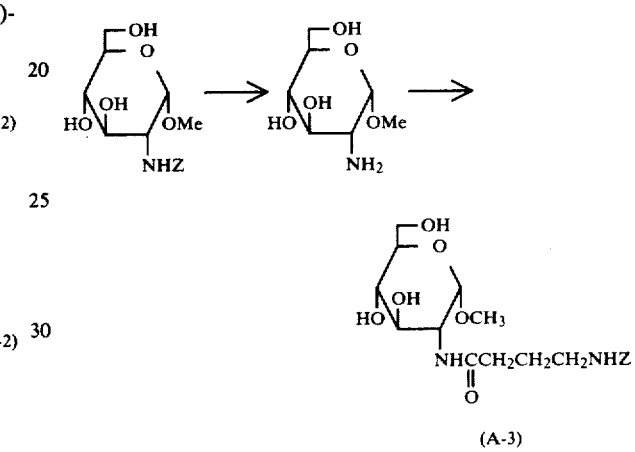

Methyl N-benzyloxycarbonyl-α-D-glucosaminide (1.0 g, 3.06 mmol.) was treated for the debenzyloxycarbonylation in the same manner as that used in Example 2, affording methyl α-D-glucosaminide.

N-Carbobenzoxy-4-aminobutyric acid (726 mg, 3.06 mmol.) was treated for the formation of an active ester thereof with N-hydroxysuccinimide (352 mg, 3.06 mmol.) and DCC (631 mg, 3.06 mmol.) in the same manner as that used in Example 7(1).

Methyl α-D-glucosaminide prepared as above was reacted with the active ester obtained above in the same manner as that described in Example 7(1). TLC of the resultant reaction mixture with a developer system of 4:1 (by volume) chloroform-methanol showed a substantially single spot at Rf 0.62 and no spot at the origin. After-treatment of the reaction mixture was carried out as in Example 7(1), yielding the compound (A-3) (846 mg) as fine plate-like crystals after recrystallization from n-propanol.

Yield: 67.1%, m.p. 160°~161° C.; $[\alpha]_D^{23} + 84.4°$ (c 0.77, methanol).

Elemental analysis: Calculated for $C_{19}H_{28}N_2O_8$, MW=412.43: C 55.33, H 6.84, N 6.79%. Found: C 55.26, H 6.68, N 6.58%.

(2) Preparation of methyl 2'-[N-[N-(2-chloroethyl)-N-nitroso-carbamoyl]amino-n-butyryl]amino-2'-deoxy-α-D-glucopyranoside (AN-3)

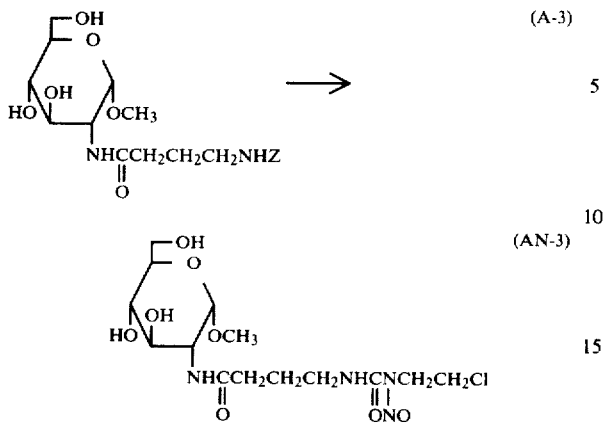

Compound (A-3) (300 mg, 0.727 mmol.) was dissolved in methanol (10 ml) and the solution was hydrogenated in the presence of Pd-black (30 mg) as catalyst under the initial hydrogen pressure of 50 psi for 6 hours to remove the benzyloxycarbonyl group. After the completion of reaction was confirmed by TLC, the catalyst was filtered off and the filtrate was concentrated to a volume of about 5 ml. To the concentrate was added triethylamine (37 mg, 0.5 moles per mole of the starting compound), then added a solution of p-nitrophenyl N-(2-chloroethyl)-N-nitroso-carbamate (398 mg, 2 moles per mole of the starting compound) in THF (5 ml) dropwise over about 15 minutes under light-shielding and the mixture was held at room temperature for further 2 hours under stirring to complete the reaction.

TLC of the reaction mixture with a developer system of 4:1 (by volume) chloroform-methanol gave a single spot at $R_f$ 0.44 for the desired product having a UV absorption and no spot at the origin. The reaction mixture was then concentrated at room temperature in vacuo, leaving a deep yellow oil. The oil was dissolved in a minimum amount of methanol required, to which an amount of isopropylether was then added to precipitate an oil. The whole was stored in a refrigerator overnight to crystallize the oil and filtered to recover the crystals which were washed with isopropyl alcohol, yielding the compound (AN-3) (214 mg) which was confirmed as a single spot in TLC.

Yield: 71.3%; m.p. 146°–148° C. (with bubbling).

$[\alpha]_D^{23} = +92.3°$ (c 0.65, methanol);

Elemental analysis: Calculated for $C_{14}H_{25}N_4O_8Cl$, MW=412.829: C 40.73, H 6.10, N 13.57, Cl 8.59%; Found: C 40.93, H 6.02, N 13.22, Cl 8.31%.

EXAMPLE 9

(1) Preparation of methyl 2-[(benzyloxycarbonyl)-L-alanyl]amino-2-deoxy-α-D-glucopyranoside (A-4)

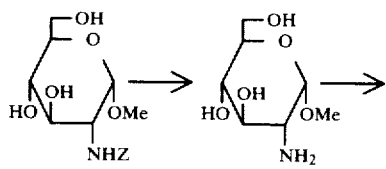

Methyl N-benzyloxycarbonyl-α-D-glucosaminide (1.0 g, 3.06 mmol.) was treated for the debenzyloxycarbonylation in the same manner as that used in the preceding Examples, yielding methyl α-D-glucosaminide. The compound was reacted with an active ester of N-carbobenzoxy-L-alanine which had been prepared from N-carbobenzoxy-L-alanine (683 mg, 3.06 mmol.), N-hydroxysuccinimide (352 mg, 3.06 mmol.) and DCC (631 mg, 3.06 mmol.) as in the preceding Examples.

After the completion of reaction was confirmed by TLC with a developer system of 4:1 (by volume) chloroform-methanol which gave a substantially single spot at $R_f$ 0.62 with no spot at the origin, the reaction mixture was after-treated as in the preceding Examples, yielding the compound (A-4) (863 mg) as fine rod-like crystals.

Yield: 70.9%; m.p. 173.5°–174° C.; $[\alpha]_D^{23} + 67.1°$ (c 0.54, methanol).

Elemental analysis: Calculated for $C_{18}H_{26}N_2O_8$, MW=398.404: C 54.26, H 6.58, N 7.03%; Found: C 54.53, H 6.65, N 6.98%.

(2) Preparation of methyl 2'-[N-[N-(2-chloroethyl)-N-nitroso-carbamoyl]-L-alanyl]amino-2'-deoxy-α-D-glucopyranoside (AN-4)

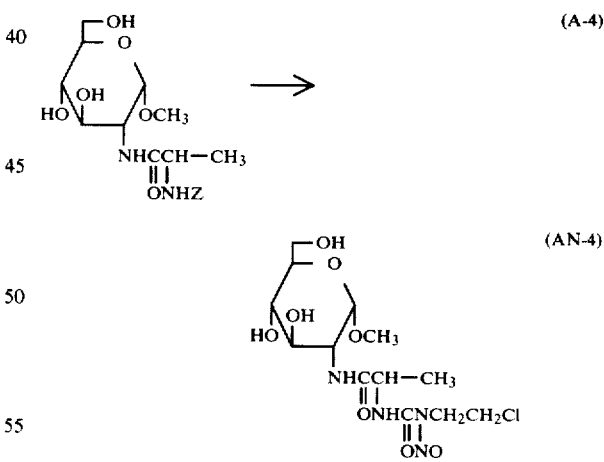

Compound (A-4) (150 mg, 0.377 mmol.) was dissolved in methanol (10 ml) and the solution was hydrogenated in the presence of Pd-black (20 mg) as catalyst under the initial hydrogen pressure of 50 psi for 6 hours to remove the benzyloxycarbonyl group. After the completion of reaction was confirmed by TLC, the catalyst was removed by spontaneous filtration and the filtrate was concentrated to a volume of about 5 ml with a partial crystallization. To the concentrate was added triethylamine (19 mg, 0.5 moles per mole of the starting compound), then added dropwise under light shielding a solution of p-nitrophenyl N-(2-chloroethyl)-N-nitroso-carbamate (412 mg, 4 moles per mole of the starting compound) in THF (5 ml) over about 15 minutes and the mixture was held at room temperature for further 3 hours under stirring to complete the reaction.

TLC of the reaction mixture with a developer system of 4:1 (by volume) chloroform-methanol gave a single spot at $R_f$ 0.58 for the desired product having a UV absorption and no spot at the origin. The reaction solution was then concentrated in vacuo at room temperature, leaving a deep yellow oil. The oil was dissolved in a minimum amount of methanol required, to which an amount of isopropylether was added to precipitate an oil. The whole was stored in a refrigerator overnight, at which the supernatant liquid was removed and the oil was washed with isopropylether several times. The oil was then dissolved in isopropyl alcohol and the solution was concentrated sufficiently to deposit a solid mass which was filtered and washed well with isopropyl alcohol, affording the compound (AN-4) (143 mg) which was confirmed as a single spot in TLC.

Yield: 95.2%; m.p. 154°–156° C. (with bubbling).
$[\alpha]_D^{23} = +104.7°$ (c 0.5, methanol).
Elemental analysis: Calculated for $C_{13}H_{23}N_4O_8Cl$, MW=398.803: C 39.15, H 5.81, N 14.05, Cl 8.89%; Found: C 38.98, H 5.94, N 14.02, Cl 8.91%.

EXAMPLE 10

(1) Preparation of methyl 3-[(benzyloxycarbonyl)-glycyl]amino-3-deoxy-α-D-mannopyranoside (A-5)

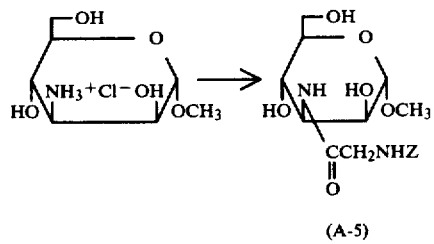

Methyl 3-amino-3-deoxy-α-D-mannopyranoside hydrochloride (500 mg, 2.18 mmol.) which was prepared by A. C. Richardson's process was dissolved in DMF (4 ml). N-Hydroxysuccinimide ester of N-carbobenzoxy-glycine (664 mg, 1.05 moles per mole of the starting compound) and triethylamine (0.91 ml, 3 moles per mole of the starting compound) were added to the solution under stirring and ice-cooling. The reaction mixture was stirred under ice-cooling for further one hour and then at room temperature overnight to complete the reaction.

TLC of the reaction mixture with a developer system of 7:1 (by volume) chloroform-methanol showed a substantially single spot at Rf 0.36 with no spot at the origin, after which the deposited triethylamine hydrochloride was removed by filtration and the filtrate was concentrated in vacuo to leave an oil. The oil was purified by a silica gel-column chromatography (silica gel: 30 g of Wako gel C-300; eluent: chloroform-methanol=9:1 by volume). Fractions corresponding to compound (A-5) were collected and concentrated in vacuo to leave an oil. The oil was allowed to stand overnight to deposit crystals, which were filtered and dried with the addition of a small amount of acetone to yield compound (A-5) as fine column-like crystals (613 mg).

Yield: 73.2%; m.p. 152°–153.5° C.; $[\alpha]_D^{22} = +39.5°$ (c 0.8, methanol);
Elemental analysis: Found: C 53.15, H 6.23, N 7.03%; Calculated for $C_{17}H_{24}N_2O_8$, MW=384.387: C 53.12, H 6.29, N 7.29%.

(2) Preparation of methyl 3'-[N-[N-(2-chloroethyl)-N-nitroso-carbamoyl]-glycyl]amino-3'-deoxy-α-D-mannopyranoside (AN-5)

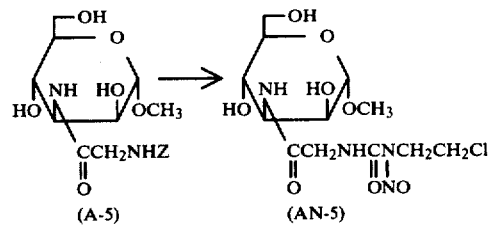

Compound (A-5) (150 mg, 0.39 mmol.) was dissolved in methanol (5 ml) and hydrogenated in the presence of Pd-black (20 mg) under the initial hydrogen pressure of 50 psi for 8 hours to remove the benzyloxycarbonyl group. The completion of reaction was confirmed by TLC, after which the catalyst was removed by filtration and the filtrate was concentrated to a volume of about 5 ml. To the concentrate triethylamine (20 ml, 0.5 moles per mole of the starting compound) was added and then a solution of p-nitrophenyl N-(2-chloroethyl)-N-nitroso-carbamate (227 mg, 2.2 moles per mole of the starting compound) in THF (5 ml) was added dropwise over about 15 minutes under light-shielding and the reaction mixture was held at room temperature for further 3 hours under stirring to complete the reaction. Then, TLC of the reaction mixture with a developer system of 4:1 (by volume) chloroform-methanol gave a main spot at Rf 0.47 for the main product showing a UV absorption and a secondary spot at Rf 0.22 for a small amount of a by-product, but substantially no spot at the origin. The reaction solution was concentrated in vacuo at room temperature to leave a deep yellow oil. The oily residue was dissolved in a minimum amount of methanol required, to which isopropylether was added to precipitate an oil. After the removal of the supernatant liquid, the oil was washed with isopropylether several times and then purified by a silica gel-column chromatography (silica gel: 10 g of Wako gel C-300; eluent: chloroform-methanol=9:1 by volume). Fractions corresponding to compound (AN-5) were collected and concentrated in vacuo to leave an oil, to which a small amount each of methanol and isopropylether was added and the mixture was concentrated in vacuo and dried with the addition of a small amount of acetone, affording pale yellow crystals (80 mg) which was confirmed as a single substance having a very hygroscopic property by TLC.

Yield: 53.3%; m.p. 145.5° C. (with bubbling).
$[\alpha]_D^{22} + 44.4°$ (c 0.5, methanol).

EXAMPLE 11

(1) Preparation of methyl 3-[(benzyloxycarbonyl)-glycyl]amino-3-deoxy-α-D-glucopyranoside (A-6)

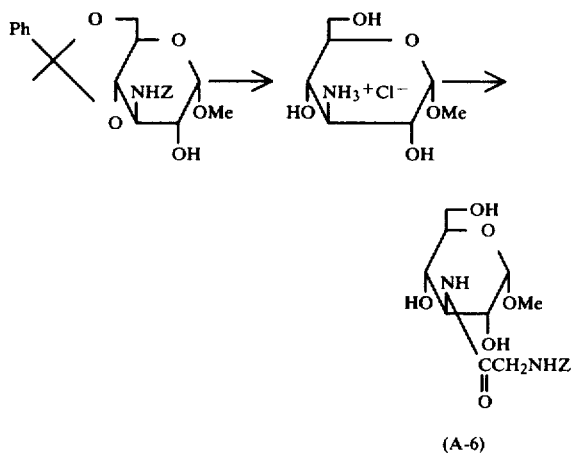

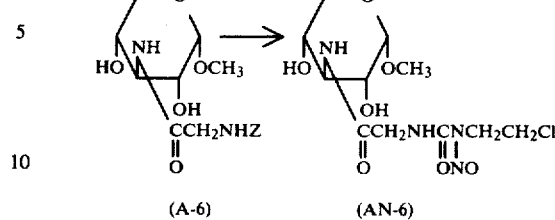

Methyl 3-(benzyloxycarbonyl)amino-4,6-O-benzylidene-3-deoxy-α-D-glucopyranoside (800 mg, 1.93 mmol.) was dissolved in a mixture of methyl cellosolve (20 ml) and dioxane (40 ml), to which was added 1N hydrochloric acid (4 ml) and the solution was hydrogenated in the presence of Pd-black (50 mg) as catalyst under the initial hydrogen pressure of 50 psi for 48 hours.

TLC of the reaction mixture with a developer system of 4:1 (by volume) chloroform-methanol gave a single spot at Rf 0.07 which was positive to ninhydrin reaction, after which the catalyst was removed by filtration and the filtrate was concentrated in vacuo to leave an oil. The oily residue was dissolved in DMF (4 ml), to which were added dropwise N-hydroxysuccinimide of N-carbobenzoxyglycine (587 mg, 1.05 moles per mole of the starting compound) and triethylamine (0.54 ml, 2 moles per mole of the starting compound) at room temperature under stirring. After the completion of addition, the reaction mixture was held under the same conditions as above overnight to complete the reaction.

TLC of the reaction mixture with a developer system of 7:1 (by volume) chloroform-methanol gave a substantially single spot at Rf 0.25 with no spot at the origin, after which the reaction solution was concentrated in vacuo to leave an oil. The oily residue was purified by a silica gel-column chromatography (silica gel: 30 g of Wako gel C-300; eluent: chloroform-methanol=9:1 by volume). Fractions corresponding to compound (A-6) were collected and concentrated in vacuo to deposit crystals which were washed with acetone, affording compound (A-6) as fine needle-like crystals (552 mg).

Yield: 74.6%; m.p. 192.5°∼193.5° C.

$[α]_D^{22} = +106.4°$ (c 0.75, methanol).

Elemental analysis: Found: C 53.73, H 6.30, N 6.94%; Calculated for $C_{17}H_{24}N_2O_8$, MW=384.378: C 53.12, H 6.29, N 7.29%.

(2) Preparation of methyl 3'-[N-[N-(2-chloroethyl)-N-nitroso-carbamoyl]-glycyl]amino-3'-deoxy-α-D-glucopyranoside (AN-6)

Compound (A-6) (220 mg, 0.572 mmol.) was dissolved in methanol (15 ml) and the solution was hydrogenated in the presence of Pd-black (20 mg) as catalyst under the initial hydrogen pressure of 50 psi for 6 hours to remove the benzyloxycarbonyl group.

TLC of the reaction mixture with a developer system of 7:1 (by volume) chloroform-methanol showed a single spot at the origin which was positive to ninhydrin reaction with no spot at Rf 0.25 for compound (A-6), after which the catalyst was removed by filtration and the filtrate was concentrated in vacuo to a volume of about 5 ml with a partial crystallization. Triethylamine (29 mg, 0.5 moles per mole of the starting compound) was added to the concentrate, to which was then added dropwise a solution of p-nitrophenyl N-(2-chloroethyl)-N-nitroso-carbamate (313 mg, 2 moles per mole of the starting compound) in THF (5 ml) over about 15 minutes under light-shielding and the reaction mixture was held under the same conditions for further 90 minutes to complete the reaction.

TLC of the reaction mixture with the same developer system as above showed a main spot at Rf 0.21 for the main product showing a UV absorption and a secondary spot for a small amount of a by-product, but substantially no spot at the origin, after which the reaction solution was concentrated in vacuo at room temperature to leave a deep yellow oil. The oily residue was dissolved in a minimum amount of methanol required, to which was added an amount of isopropylether to precipitate an oil. The whole was stored in a refrigerator overnight, after which the supernatant liquid was removed and the oily residue was washed with isopropylether several times and crystallized from isopropyl alcohol to yield compound (AN-6) (155 mg).

Yield: 70.4%; m.p. 166°∼168° C. (with bubbling).

$[α]_D^{23} = +109.1°$ (c 0.5, methanol).

EXAMPLE 12

(1) Preparation of methyl 2-[(benzyloxycarbonyl)-L-seryl]amino-2-deoxy-α-D-glucopyranoside (A-7)

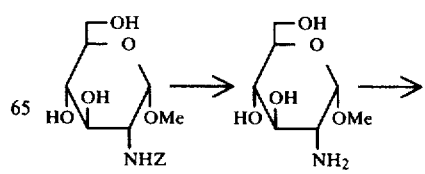

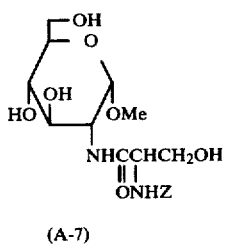

(A-7)

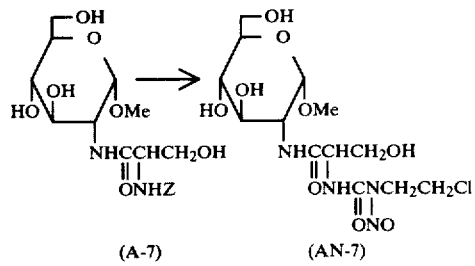

Methyl N-benzyloxycarbonyl-α-D-glucosaminide (1.37 g, 4.18 mmol.) was treated for debenzyloxycarbonylation in the same manner as that used in preceding Examples to yield methyl α-D-glucosaminide as an oily residue in a quantitative yield.

N-Carbobenzoxy-L-serine commercially available (1.00 g, 4.18 mmol.) and H-hydroxysuccinimide (481 mg, 4.18 mmol.) were dissolved in dioxane (5 ml) and DCC (862 mg, 4.18 mmol.) was added to the solution under stirring and ice-cooling. The reaction was continued under the same conditions for further one hour and then at room temperature for 2 hours, yielding a solution of the desired active ester.

Methyl α-D-glucosaminide prepared as above was dissolved in DMF (4 ml) and triethylamine (1.15 ml, 8.30 mmol.) was added to the solution, to which was then added dropwise, under stirring and ice-cooling, the solution of the active ester of N-hydroxysuccinimide with N-carbobenzoxy-L-serine prepared as above which had been filtered to remove dicyclohexylurea deposited. The reaction was continued under ice-cooling for further one hour and then at room temperature for 2 hours.

TLC of the reaction mixture with a developer system of 4:1 (by volume) chloroform-methanol showed a single spot at Rf 0.44 with a weak residual spot at the origin, after which the reaction solution was concentrated in vacuo with the deposition of a further amount of dicyclohexylurea. The latter was removed by filtration and the filtrate was again concentrated in vacuo to leave a pale yellow oil. The oily residue was isolated and purified by a silica gel-column chromatography (silica gel: 60 g of Wako gel C-300; eluent: chloroform-methanol=7:1 by volume). Fractions containing the object compound were collected and concentrated in vacuo to yield a white crystalline residue which was recrystallized from isopropyl alcohol, affording compound (A-7) as white fine needles (1.255 g).

Yield: 72.4%; m.p. 179.5°∼180.5° C.

$[\alpha]_D^{23} = +76.5°$ C. (c 0.5, methanol).

Elemental analysis: Calculated for $C_{18}H_{26}N_2O_9$, MW=414.404: C 52.17, H 6.32, N 6.76%; Found: C 51.94, H 6.11, N 6.50%.

(2) Preparation of methyl 2'-[N-[N-(2-chloroethyl)-N-nitroso-carbamoyl]-L-seryl]amino-2'-deoxy-α-D-glucopyranoside (AN-7)

Compound (A-7) (250 mg, 0.60 mmol.) was dissolved in methanol (12 ml) and the solution was hydrogenated in the presence of Pd-black (20 mg) as catalyst under the initial hydrogen pressure of 50 psi for 4 hours to remove the benzyloxycarbonyl group.

After the completion of reaction was confirmed by TLC, the catalyst was removed by filtration and the filtrate was concentrated in vacuo to a volume of about 5 ml with a partial crystallization. Triethylamine (30 mg, 0.5 moles per mole of the starting compound) was added to the concentrate, to which was then added dropwise over about 15 minutes a solution of p-nitrophenyl N-(2-chloroethyl)-N-nitroso-carbamate (821 mg, 5 moles per mole of the starting compound) in THF (10 ml) and the reaction was continued for further 3 hours.

TLC of the reaction mixture showed a main spot at Rf 0.50 for the main product showing a UV absorption and a secondary spot at Rf 0.19 for a small amount of a by-product with a trace spot of Rf 0.04 for the starting compound. The reaction solution was then concentrated in vacuo with the deposition of unreacted excess p-nitrophenyl N-(2-chloroethyl)-N-nitroso-carbamate and filtered to remove the deposited starting material and this treatment was repeated once. Then, the final concentration of the filtrate in vacuo gave a pale yellow oily residue. The residue was dissolved in a minimum amount of methanol required and an amount of isopropylether was added to the solution to precipitate an oil. The whole was stored in a refrigerator overnight, after which the supernatant liquid was removed and the oil solidified was dissolved in methanol. The solution was concentrated in vacuo to leave an oil which was purified by a silica gel-column chromatography (silica gel: 10 g of Wako gel C-300; eluent: chloroform-methanol=3:1 by volume). Fractions corresponding to the main product were collected and concentrated in vacuo to leave an oil which was crystallized from ethanol, yielding compound (AN-7) as white needles (132 mg).

Yield: 52.7%; m.p. 150°∼152° C. (with bubbling).

EXAMPLE 13

(1) Preparation of 1-[(benzyloxycarbonyl)-glycyl]amino-1-deoxy-β-D-glucopyranose (A-8)

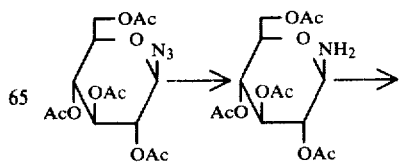

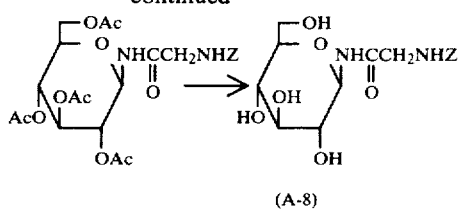

(A-8)

2,3,4,6-Tetra-O-acetyl-β-D-glucopyranosyl azide (1.56 g, 4.18 mmol.) was dissolved in ethanol (50 ml). The resulting solution was subjected to catalytic hydrogenation in the presence of Raney nickel T-4 catalyst (1.5 ml) under the initial hydrogen pressure of 50 psi for 24 hours to reduce the azide group into amino group. From the reaction solution was taken out a portion thereof which was subjected to TLC on silica gel developed with a developer system of benzene-acetone (9:1 by volume). According to this TLC analysis, the completion of the reaction was confirmed by detecting whether the reduction product gave a ninhydrin-positive single spot of Rf 0.18. After this, the reaction solution was filtered to remove the catalyst, and the filtrate was concentrated under reduced pressure, affording the O-acetylglucosylamino compound as the white crystalline residue. This residue was taken up into dioxane (10 ml), and to the resultant solution were added N-carbobenzoxy-glycine N-hydroxy-succinimide active ester (1.27 g, 1.05 moles per mole of the starting compound) and triethylamine (0.58 ml, 1 mole per mole of the starting compound). The mixture was held at room temperature for 6 hours to effect the reaction for formation of the condensation product.

The reaction solution so obtained was analyzed by TLC (with the developer system same as above) to detect that the condensation product giving a ninhydrin-negative single spot at Rf 0.15 was formed and that a part of the O-acetylglucosylamino compound still remained unreacted. To the reaction solution were then added a further amount of the N-carbobenzoxy-glycine active ester (365 mg, 0.3 moles per mole of the starting compound) and a further amount of triethylamine (0.17 ml, 0.3 moles per mole of the starting compound), followed by continued reaction at room temperature for 3 hours to complete the reaction.

After the complete consumption of the starting O-acetylglucosylamino compound was confirmed, the reaction solution was concentrated under reduced pressure, giving an oily residue. This residue was taken up into chloroform (150 ml) and the solution was washed twice with water (200 ml×2), dried over anhydrous sodium sulfate and then concentrated under reduced pressure to afford the O-acetylglucosyl-benzyloxycarbonylamino compound as an oily residue.

This compound was dissolved in a mixed solvent of dioxane-methanol (25 ml/25 ml), and to the resultant solution was added dropwise 35 ml of a solution of 0.1N sodium methoxide in methanol under ice-cooling and stirring. The reaction mixture was held at room temperature for 40 minutes to effect the deacetylation. The reaction mixture was analysed by TLC on silica gel developed with chloroform-methanol (7:1 by volume). After it was confirmed by this TLC that the starting compound giving a single spot at Rf 0.8 disappeared and that the deacetylated product (A-8) giving a single spot at Rf 0.08 was formed in the reaction mixture, the reaction mixture was neutralized with Amberlite IR-120 resin (H+ form). The resin was filtered off out of the reaction mixture and the filtrate was concentrated under reduced pressure to give a foamed oily residue. Crystallization of this residue from acetone gave 1.155 g of the desired compound (A-8).

Yield: 74.6% (based on the azide compound).
m.p. 162°~164° C.; $[\alpha]_D^{23}$ −12.9° (c 1, H$_2$O).
Elemental analysis:
Calculated for C$_{14}$H$_{22}$N$_2$O$_8$, MW=370.352: C 51.89, H 5.99, N 7.56% Found: C 52.17, H 5.99 N 7.34%.

(2) Preparation of 1'-[N-[N-(2-chloroethyl)-N-nitrosocarbamoyl]-glycyl]amino-1'-deoxy-β-D-glucopyranose (AN-8)

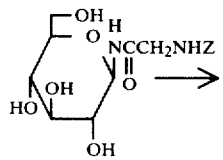

(A-8)

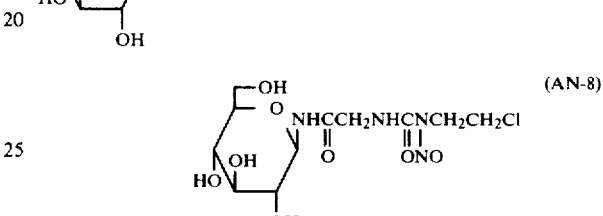

(AN-8)

Compound (A-8) (230 mg, 0.62 mmol.) was dissolved in methanol (15 ml) and the solution was admixed with 0.1N hydrochloric acid (0.7 ml), followed by hydrogenation in the presence of Pd-black (30 mg) as catalyst under the initial hydrogen pressure of 50 psi for 4 hours to remove the benzyloxycarbonyl group (Z). After completion of the reaction was confirmed by TLC, the catalyst was removed by filtration of the reaction mixture and the filtrate was concentrated under reduced pressure by some water was still remaining in the residue. The residue was admixed with triethylamine (0.13 ml), followed by neutralization with HCl.

The solution so neutralized was then concentrated and distilled azeotropically with ethanol, affording a white crystalline residue. This residue was washed several times with small volumes of chloroform to remove the triethylamine hydrochloride therefrom, and the washed residue was dissolved in methanol (5 ml). To the solution was added dropwise triethylamine (31 mg, 0.5 moles per mole of the compound (A-8) and then added dropwise over about 15 minutes a solution of p-nitrophenyl N-(2-chloroethyl)-N-nitroso-carbamate (340 mg, 2 moles per mole of the starting compound) in THF (5 ml) under stirring in dark. The reaction was continued for further 2 hours at room temperature.

The reaction solution was analyzed by TLC on silica gel with a developer system of chloroform-methanol (4:1 by volume) to show that the original spot for the starting compound disappeared substantially and that a single spot appeared at Rf 0.15 for the desired product having a UV absorption, with spots for some non-identified by-products. The reaction solution was then concentrated under reduced pressure to leave a deep yellow oil which was subsequently dissolved in a minimum volume of methanol required. The methanolic solution was admixed with a volume of isopropyl ether to deposit the oil. The whole mixture was stored in a refrigerator overnight. The supernatant liquid as formed was separated off and the remaining oil was washed with isopropyl ether several times. The oil was purified by column-chromatography on silica gel (Wako-Gel C-300, 5 g) with a developer system of chloroform-methanol (3:1 by volume). Thus, the eluate from the silica gel column was collected in fractions, and the fractions containing the desired product which showed a UV absorption were combined together and concentrated in vacuo to give a crystalline residue. This residue was washed with chloroform to afford 148 mg of the desired compound (AN-8) as light yellow crystals.

Yield: 64.3% (61.3% as the monohydrate).
m.p. 110°~112° C. (with foaming).
$[\alpha]_D^{23} = +0.7°$ (c 0.3, $H_2O$).

Elemental analysis: Calculated for $C_{11}H_{19}N_4O_8Cl \cdot H_2O$, MW=388.767; C 33.98, H 5.44, N 14.41, Cl 9.12%; Found: C 33.98, H. 5.39, N 14.62, Cl 9.26%.

EXAMPLE 14

(1) Preparation of (1/2,6)-[(N-benzyloxycarbonyl)-glycyl]-amino-2,6-hexanediol (A-9)

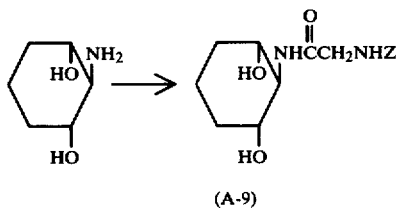

(A-9)

1,3/2N-Aminocyclohexanediol (1.0 g, 7.62 mmol.) was dissolved in DMF (12 ml) and the solution was admixed with N-carbobenzoxy-glycine N-hydroxysuccinimide active ester (2.21 g, 1 mole per mole of the starting compound) and triethylamine (1.0 ml, 1 mole per mole of the starting compound) under ice-cooling, followed by stirring for 2 hours to effect the reaction for formation of the compound (A-9).

The reaction solution as analyzed by TLC with a developer system of benzene-ethanol (5:1 by volume). After it was confirmed by this TLC that the original spot for the starting compound disappeared substantially while the spot at Rf 0.39 for the desired product (A-9) occurred together with a spot at Rf 0.53 for a slight amount of non-identified by-product, the reaction solution was concentrated under reduced pressure to leave a white crystalline residue. The crystalline product was removed by filtration and washed with a large volume of acetone, affording 1.527 g of the compound (A-9) as fine prism-like crystals.

On the other hand, the filtrate obtained from the above filtration was concentrated under reduced pressure to give an oil which was then purified by column-chromatography on silica gel (Wako gel C-300, 30 g) developed with a developer system of benzene-ethanol (7:1 by volume). The eluate from the silica gel column was collected in fractions, and the fractions containing the compound (A-9) were combined together and concentrated in vacuo to give a white crystalline residue. This residue was washed with acetone to afford 559 mg of the compound (A-9).

The above two crops were combined and recrystallized from acetone to yield 1.903 g of the compound (A-9).

Yield: 77.5%; m.p. 173.0°~174.0° C.

Elemental analysis: Calculated for $C_{16}H_{22}N_2O_5$, MW=332.352: C 59.61, H 6.87, N 8.69%; Found: C 59.35, H 6.79, N 8.49%.

(2) Preparation of (1'/2',6')-1'-[N-[N-(2-chloroethyl)-N-nitroso-carbamoyl]-glycyl]amino-2',6'-cyclohexanediol (AN-9)

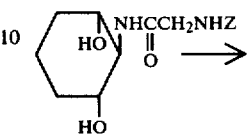

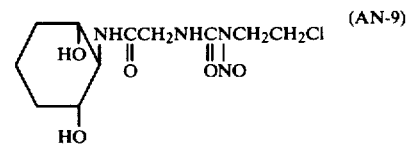

Compound (A-9) (255 mg, 0.83 mmol.) was dissolved in methanol (15 ml) and the solution was subjected to catalytic hydrogenation in the presence of Pd-black catalyst (20 mg) under the initial hydrogen pressure of 50 psi for 4 hours. After the completion of the reaction was confirmed by TLC, the reaction mixture was filtered to remove the catalyst, and the filtrate was concentrated under reduced pressure to a volume of about 5 ml with a partial crystallization. To the concentrate was added triethylamine (42 mg, 0.5 moles per mole of the starting compound) and then added dropwise over about 15 minutes a solution of p-nitrophenyl N-(2-chloroethyl)-N-nitroso-carbamate (455 mg, 2 moles per mole of the starting compound) in THF (6 ml) under stirring in dark, followed by continued reaction at room temperature for 2 hours.

The reaction solution was analyzed by TLC with a developer system of benzene-ethanol (5:1 by volume). After it was confirmed by this TLC that the original spot for the starting compound disappeared substantially and a spot occurred at Rf 0.31 to show formation of a substantially single reaction product having a UV absorption, the reaction solution was concentrated under reduced pressure to leave a deep yellow oily residue. This oil was taken up into a minimum volume of ethanol required and the solution was admixed with a volume of isopropyl ether to deposit the oil. The whole mixture was stored in a refrigerator overnight, and the supernatant liquid as formed was separated off and the remaining semi-solidified residue was washed with isopropyl ether. The washed material was dissolved in a volume of ethanol, followed by concentration under reduced pressure to give an oily residue. This oil was crystallized from n-propanol and the crystals were washed with chloroform to afford 137 mg of the compound (AN-9).

Yield: 53.7%; m.p. 145°~147° C. (with foaming).

Elemental analysis: Calculated for $C_{11}H_{19}N_4O_5Cl$, MW=322.751: C 40.93, H 5.93, N 17.36, Cl 10.99%; Found: C 40.60, H 5.84, N 17.02, Cl 10.94%.

EXAMPLE 15

(1) Preparation of (1/2,6)-[(N-benzyloxycarbamoyl)-n-butyryl]-amino-2,6-cyclohexanediol (A-10)

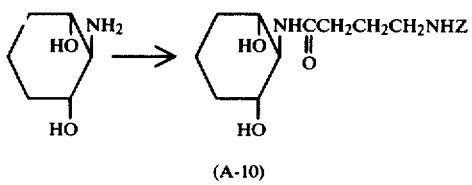

A commercially available N-carbobenzoxy-4-aminobutyric acid (904 mg, 3.81 mmol.) and N-hydroxysuccinimide (438 mg, 3.81 mmol.) were dissolved in dioxane (5 ml), and to the resultant solution was added dicyclohexylcarbodiimide (DCC) (786 mg, 3.81 mmol.) under ice-cooling and stirring. The whole mixture was held for 1 hour as such and then held at room temperature for 2 hours to effect the reaction for formation of the active ester of the N-protected amino acid.

1,3/2N-aminocyclohexanediol (500 mg, 3.81 mmol.) was taken up into DMF (6 ml), and the resultant solution was admixed with triethylamine (0.53 ml, 3.81 mmol.), followed by dropwise addition, under ice-cooling and stirring, of a solution of the above-mentioned N-protected amino acid active ester from which had been removed the dicyclohexylurea. The whole mixture was held for 1 hour as such to effect the reaction, followed by continued reaction at room temperature for 2 hours under stirring.

The reaction solution was analyzed by TLC with a developer system of chloroform-methanol (4:1 by volume). Then, it was confirmed by this TLC that the original spot for the starting compound was still remaining slightly and a spot occurred at Rf 0.81 to show formation of a single reaction product. The reaction solution was concentrated under reduced pressure to leave a white crystalline residue. The whole mixture was admixed with a volume of acetone and filtered. The solid so collected was washed with a large volume of acetone to afford crude crystals of the compound (A-10). Recrystallization of this product from ethanol gave 830 mg of the purified compound (A-10).

Yield: 62.1%: m.p. 167.5°~168.5° C.

Elemental analysis: Calculated for $C_{18}H_{26}N_2O_5$, MW=350.404: C 61.69, H 7.48, N 8.00%; Found: C 61.94, H 7.53, N 8.08%.

(2) Preparation of (1'/2',6')-1'-[N-[N-(2-chloroethyl)-N-nitroso-carbamoyl]amino-n-butyryl]amino-2',6'-cyclohexanediol (AN-10)

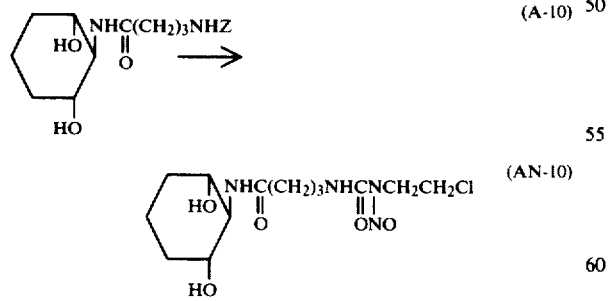

Compound (A-10) (200 mg, 0.57 mmol.) was dissolved in methanol (20 ml) and the solution was subjected to catalytic hydrogenation in the presence of Pd-black catalyst (20 mg) under the initial hydrogen pressure of 50 psi at room temperature for 4 hours to effect removal of the benzyloxycarbonyl group from the compound (A-10). After the completion of the N-deprotecting reaction was confirmed by TLC, the reaction mixture was filtered to remove the catalyst, and the filtrate was concentrated under reduced pressure to a volume of about 5 ml. To the concentrated reaction solution was added triethylamine (29 mg, 0.5 moles per mole of the starting compound) and then added dropwise over about 15 minutes a solution of p-nitrophenyl N-(2-chloroethyl)-N-nitroso-carbamate (312 mg, 2 moles per mole of the starting compound) in THF (5 ml) under stirring in dark, followed by continued reaction at room temperature for 1 hour.

The reaction solution was analyzed by TLC on silica gel with a developer system of chloroform-methanol (4:1 by volume), and it was then confirmed by this TLC that the original spot for the starting compound disappeared and a spot occurred at Rf 0.77 for the single reaction product having a UV absorption. The reaction solution was concentrated under reduced pressure to leave a deep yellow oily residue which was then dissolved in a minimum volume of ethanol required. The resulting solution was admixed with a volume of isopropyl ether to deposit an oil, and the whole mixture was subsequently stored in a refrigerator overnight. The supernatant liquid as formed was separated off, and the remaining semi-solid was washed with isopropyl ether and dissolved in a volume of ethanol. The ethanolic solution was concentrated under reduced pressure with partial crystallization, followed by addition of a volume of acetone and further concentration in vacuo to complete the crystallization. The crystalline product so obtained was washed with isopropyl alcohol to afford 124 mg of the desired compound (AN-10).

Yield: 61.9%, m.p. 135°~136° C. (with foaming).

Elemental analysis: Calculated for $C_{13}H_{23}N_4O_5Cl$, MW=350.803: C 44.51, H 6.61, N 15.97, Cl 10.11%; Found: C 44.61, H 6.43, N 15.57, Cl 10.47%.

EXAMPLE 16

Preparation of methyl 2'-[[N-[N-(2-chloroethyl)-N-nitroso-carbamoyl]-glycyl]-glycyl]amino-2'-deoxy-α-D-glucopyranoside (AN-11)

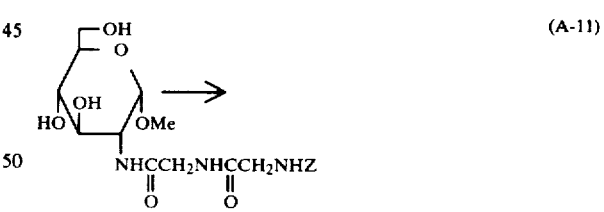

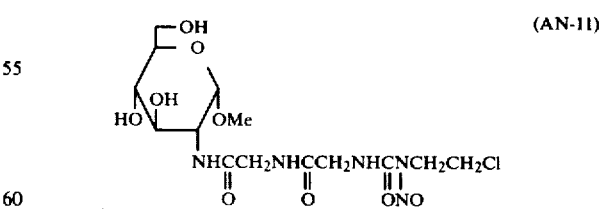

Methyl 2-[[(benzyloxycarbonyl)-glycyl]-glycyl]amino-2-deoxy-α-D-glucopyranoside (A-11) (240 mg, 0.544 mmol.) was dissolved in a mixed solvent of dioxane (10 ml) and methanol (15 ml), and the resultant solution was subjected to catalytic hydrogenation in the presence of Pd-black catalyst (30 mg) under the initial hydrogen pressure of 50 psi for 4 hours to effect removal of the benzyloxycarbonyl group. After the completion of the N-deprotecting reaction was confirmed by TLC, the reaction mixture was filtered to remove the catalyst. The filtrate was concentrated under reduced pressure to afford a crystalline residue which was then suspended in methanol (5 ml). To the suspension in methanol was added dropwise triethylamine (27.5 mg, 0.5 moles per mole of the starting compound) and then added dropwise over about 10 minutes a solution of p-nitrophenyl N-(2-chloroethyl)-N-nitrosocarbamate (268 mg, 1.8 moles per mole of the starting compound) in THF (5 ml) under stirring in dark, followed by continued reaction for 90 minutes.

The reaction solution was analyzed by TLC on silica gel with a developer system of chloroform-methanol (3:1 by volume). After it was confirmed by this TLC that the original spot for the starting compound disappeared while a spot occurred at Rf 0.57 for the desired product, together with a spot at Rf 0.15 for a slight amount of the by-product, the reaction solution was concentrated under reduced pressure, affording a semisolid residue. This residue was dissolved in a minimum volume of methanol requred and admixed with a volume of isopropyl ether, followed by storing in a refrigerator overnight. The supernatant liquid as formed was separated off and the semi-solid residue was dried under reduced pressure to give a light yellow solid. This solid was washed with isopropyl alcohol and then with chloroform to give 124 mg of the desired compound (AN-11) as a white solid.

Yield: 51.6%; m.p. 172.5° ~174.5° C. (with foaming). $[\alpha]_D^{24}+87.4°$ (c 0.54, DMF).

Elemental analysis: Calculated for $C_{14}H_{24}N_5O_9Cl$, MW=441.829: C 38.06, H 5.45, N 15.85, Cl 8.03%; Found: C 38.22, H 5.31, N 16.20, Cl 8.17%.

EXAMPLE 17

Preparation of (1'/2',6')-1'-[N-[N-(2-chloroethyl)-N-nitroso-carbamoyl]-β-alanyl]amino-2',6'-cyclohexanediol (AN-12)

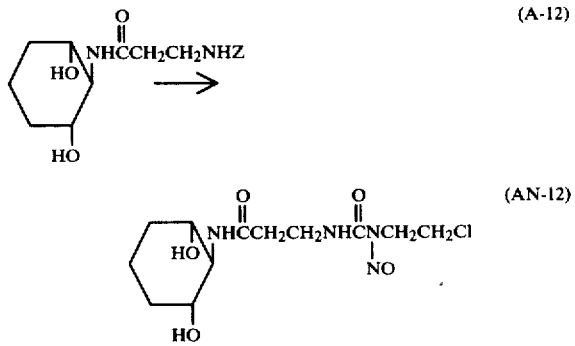

(1/2,6)-[(Benzyloxycarbonyl)-β-alanyl]amino-2,6-cyclohexanediol (A-12) (310 mg, 0.922 mmol.) was dissolved in methanol (15 ml) and the solution was subjected to catalytic hydrogenation in the presence of Pd-black catalyst (30 mg) under the initial hydrogen pressure of 50 psi for 4 hours to effect removal of the benzyloxycarbonyl group. After the completion of the N-deprotecting reaction was confirmed by TLC, the reaction mixture was filtered to remove the catalyst. The filtrate was concentrated under reduced pressure to a volume of about 5 ml with a partial crystallization. To the concentrated solution with the crystals deposited was added dropwise triethylamine (46.6 mg, 0.5 moles per mole of the starting compound) and then added dropwise a solution of p-nitro-phenyl N-(2-chloroethyl)-N-nitroso-carbamate (454 mg, 1.8 moles per mole of the starting compound) in THF (5 ml) under stirring in dark, followed by continued reaction for 90 minutes.

The reaction solution was analyzed by TLC on silica gel with a developer system of benzene-ethanol (5:1 by volume). Then, it was confirmed by this TLC that the original spot for the starting compound disappeared substantially while a spot occurred at Rf 0.30 to show the formation of substantially a single reaction product. The reaction solution was concentrated under reduced pressure to leave a deep yellow oily residue which was then taken up into a minimum volume of methanol required. The methanolic solution was admixed with a volume of isopropyl ether to deposit the oil, and the whole was stored in a refrigerator overnight. The supernatant liquid as formed was separated off and the remaining oil was purified by column-chromatography on silica gel (Wako gel C-300, 10 g) developed with a solvent system of chloroform-ethanol (8:1 by volume). Thus, the eluate from the silica gel column was collected in fractions, and the fractions containing the desired product (AN-12) were combined together and concentrated under reduced pressure to affort a light yellow crystalline residue. This residue was washed with isopropyl alcohol and then with chloroform to give 247 mg of the compound (AN-12).

Yield: 79.6%, m.p. 137°~138° C. (with foaming).

Elemental analysis: Calculated for $C_{12}H_{21}N_4O_5Cl$, MW=336.777: C 42.79, H 6.29, N 16.64, Cl 10.53%; Found: C 42.84, H 6.08, N 16.29, Cl 10.86%.

EXAMPLE 18

(1) Preparation of methyl 2-[(benzyloxycarbonyl)-D-alanyl]amino-2-deoxy-α-D-glucopyranoside (A-13)

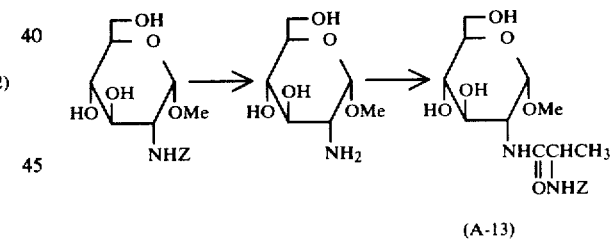

Methyl N-benzyloxycarbonyl-α-D-glucosaminide (1.47 g, 4.49 mmol.) was subjected to the debenzyloxcarbonylation in the same manner as in Example 17 above to give methyl α-D-glucosaminide as an oil in a quantitative yield.

A commercially available N-carbobenzoxy-D-alanine (1.00 g, 4.49 mmol.) and N-hydroxysuccinimide (516 mg, 4.49 mmol.) were dissolved in dioxane (5 ml), and to the resulting solution was added dicyclohexylcarbodiimide (924 mg, 4.49 mmol.) under ice-cooling and stirring. The mixture was held for 1 hour as such and then for 2 hours at room temperature to effect the reaction for formation of the active ester of the N-protected alanine.

The methyl α-D-glucosaminide prepared as above was dissolved in DMF (4 ml), and to the solution was added dropwise triethylamine (0.62 ml, 1 mole per mole of the methyl glucosaminide) and then added dropwise under ice-cooling and stirring a solution of the above prepared N-carbobenzoxy-D-alanine active ester in dioxane from which the dicyclohexylurea had been removed. The whole mixture was held for 1 hour under ice-cooling and then for 2 hours at room temperature to effect the reaction.

The reaction solution was analyzed by TLC on silica gel with a developer system of chloroform-methanol (4:1 by volume), and it was confirmed by this TLC that the original spot for the starting compound was still remaining slightly but a spot occurred at Rf 0.64 for the single reaction product. The reaction solution was concentrated under reduced pressure and the concentrated solution was filtered to remove the dicyclohexylurea which deposited once more. The concentrate was further concentrated in vacuo to leave a light yellow oily residue which was then purified by column-chromatography on silica gel (Wako gel C-300, 60 g) developed with a solvent system of chloroformmethanol (7:1 by volume). Thus, the eluate from the silica gel column was collected in fractions, and the fractions containing the desired product were combined together and concentrated in vacuo to afford a white crystalline residue. Recrystallization of this residue from isopropyl alcohol gave 1349 mg of the compound (A-13).

Yield: 75.4%; m.p. 162.5°~163.0° C.
$[\alpha]_D^{24}+97.4°$ (c 0.95, methanol).

Elemental analysis: Calculated for $C_{18}H_{26}N_2O_8$, MW=398.404: C 54.26, H 6.58, N 7.03%; Found: C 54.45, H 6.54, N 7.05%.

(2) Preparation of methyl 2'-[N-[N-(2-chloroethyl)-N-nitroso-carbamoly]-D-alanyl]amino-2'-deoxy-α-D-glucopyranoside (AN-13)

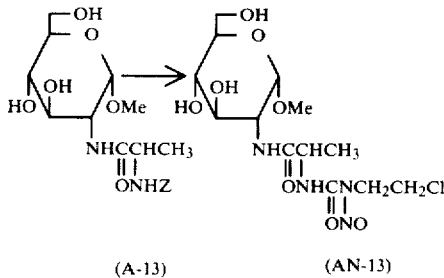

(A-13)  (AN-13)

Compound (A-13) (330 mg, 0.828 mmol.) was dissolved in methanol (20 ml) and the solution was subjected to catalytic hydrogenation in the presence of Pd-black catalyst (30 mg) under the initial hydrogen pressure of 50 psi for 4 hours to effect the debenzyloxycarbonylation. After the completion of the N-deprotecting reaction was confirmed by TLC, the reaction mixture was filtered to remove the catalyst. The filtrate was concentrated under reduced pressure to a volume of about 5 ml with partial crystallization. To the resulting concentrate was added dropwise triethylamine (41.9 mg) and then added dropwise over 10 minutes a solution of p-nitrophenyl N-(2-chloroethyl)-N-nitrosocarbamate (1020 mg, 4.5 moles per mole of the starting compound) in THF (10 ml) under stirring in dark, followed by continued reaction for 3 hours.

The reaction solution was analyzed by TLC on silica gel with a developer system of chloroform-methanol (4:1 by volume), and it was confirmed by this TLC that the original spot for the starting compound was still remaining slightly but a spot occurred at Rf 0.65 to show the formation of substantially a single reaction product. The reaction solution was concentrated under reduced pressure to give a deep yellow oily residue which had been partially crystallized. This residue was taken up into a minimum volume of methanol required and the solution was admixed with a volume of isopropyl ether to deposit an oil. The whole mixture was stored in a refrigerator overnight, and the supernatant liquid as formed was separated off and the substantially crystallized residue was washed with isopropyl ether several times. The washed material was dissolved in methanol completely and the solution was concentrated in vacuo to leave a light yellow crystalline residue which was then washed with isopropyl alcohol and with chloroform to afford 197 mg of the compound (AN-13).

Yield: 59.4%; m.p. 156°~158° C. (with foaming).
$[\alpha]_D^{22}+51.0°$ (c 0.4, methanol).

Elemental analysis: Calculated for $C_{13}H_{23}N_4O_8Cl$, MW=398.803: C 39.15, H 5.81, N 14.05, Cl 8.89%; Found: C 38.76, H 5.60, N 14.11, Cl 8.84%.

EXAMPLE 19

(1) Preparation of 2-[(benzyloxycarbonyl)-glycyl-]amino-2-deoxy-D-glucopyranose (A-14)

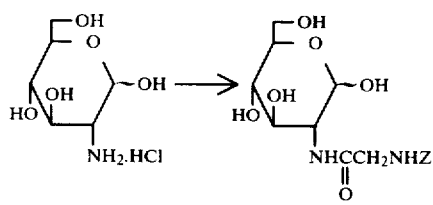

(A-14)

Glucosamine hydrochloride (1.00 g, 4.35 mmol.) was dissolved in a mixture of DMF (8 ml) and triethylamine (2.4 ml, 4 moles per mole of the starting compound), when triethylamine hydrochloride deposited as solid. To the admixture obtained was added dropwise a solution of N-carbobenzoxy-glycine N-hydroxysuccinimide active ester (1.05 moles per mole of the starting compound) in dioxane (5 ml) under ice-cooling and stirring. The whole mixture was held for 1 hour as such and then at room temperature for 2 hours under stirring for the reaction.

The reaction solution was analyzed by TLC on silica gel with a developer system of chloroform-methanol (3:1 by volume), and it was confirmed by this TLC that the original spot for the starting compound was still remaining slightly but a spot occurred at Rf 0.45 for the desired reaction product, together with a spot at Rf 0.73 for an amount of non-identified by-product. The reaction solution was concentrated under reduced pressure and the resulting light yellow oily residue was purified by column-chromatography on silica gel (Wako gel C-300, 60 g) developed with a solvent system of chloroform-methanol (3:1 by volume). For the isolation of the desired product, the eluate from the silica gel column was collected in fractions, and the fractions containing the desired product were combined together and concentrated in vacuo to give a white crystalline residue. This residue was well washed with acetone to afford crude crystals of the compound (A-14) which was then recrystallized from isopropyl alcohol. The compound (A-14) (940 mg) was obtained as very hygroscopic white crystals.

Yield: 58.3%; m.p. 178°~180.5° C.

[α]$_D^{23}$ = +34.5° (c 0.5, H$_2$O).

Elemental analysis: Calculated for C$_{16}$H$_{22}$N$_2$O$_8$·H$_2$O, MW=388.368: C 49.48, H 6.23, N 7.21%; Found: C 49.77, H 6.06, N 7.45%.

(2) Preparation of 2'-[N-[N-2-chloroethyl)-N-nitrosocarbamoyl]-glycyl]amino-2'-deoxy-D-glucopyranose (AN-14).

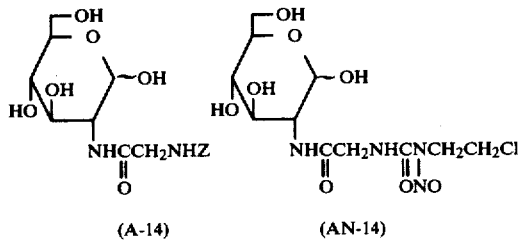

Compound (A-14) (150 mg, 0.386 mmol.) was dissolved in methanol (15 ml) and the solution was hydrogenated in the presence of Pd-black (20 mg) as catalyst under the initial hydrogen pressure of 50 psi overnight. The catalyst was removed by filtration and the reaction solution was concentrated in vacuo to a volume of about 5 ml. To the concentrate triethylamine (39 mg, 0.5 moles per mole of the starting compound) was added and then a solution of p-nitrophenyl N-(2-chloroethyl)-N-nitroso-carbamate (232 mg, 2.2 moles per mole of the starting compound) in THF (5 ml) was added dropwise over about 15 minutes under stirring and light-shielding and the reaction mixture was held at room temperature for further 3 hours to complete the reaction. Then, the reaction mixture was concentrated in vacuo at room temperature to leave a deep yellow oil. The oily residue was dissolved in a minimum amount of methanol required, to which an amount of isopropylether was added to precipitate an oil. The whole was stored in a refrigerator, after which the supernatant liquid was removed and the oil was washed with isopropylether several times and purified by a silica gel-column chromatography (silica gel: 10 g of Wako gel C-300; eluent: chloroform-methanol=8:1 by volume). Fractions corresponding to compound (AN-14) were collected, concentrated in vacuo and dried in vacuo, affording compound (AN-14) as a very hygroscopic white solid (66 mg).

Yield: 46.1%; [α]$_D^{20}$ + 16.2° (c 0.5, methanol).

What I claim is:

1. Nitrosourea derivatives of formula (I):

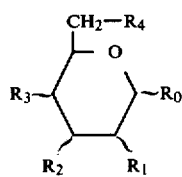

wherein R$_o$ represents —OH or —OC$_m$H$_{2m+1}$ where m is an integer of 1 to 3 and one of R$_1$, R$_2$, R$_3$ and R$_4$ represents

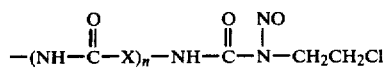

where X is

or an alkylene group of 1 to 3 carbon atoms, n is an integer of 1 to 3 and Y is the group on the α-carbon atom of an α-amino acid and each of the remaining three represents —OH; or wherein R$_o$ represents

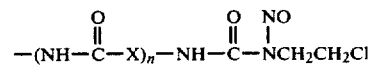

and R$_1$, R$_2$, R$_3$ and R$_4$ each represent —OH.

2. Nitrosourea derivatives as claimed in claim 1 wherein the monosaccharide skeleton in formula (I) takes a configuration selected from the group consisting of glucose, mannose, galactose, talose, idose, gulose, altrose and allose.

3. Nitrosourea derivatives as claimed in claim 1 wherein Y is the group on the α-carbon atom of an α-amino acid selected from the group consisting of alanine, phenylalanine, serine, tryptophan, methionine, cysteine, tyrosine, valine, leucine, isoleucine, threonine, aspartic acid, asparagine, glutamic acid, glutamine, lysine, hydroxylysine, histidine and arginine and di- and poly-peptides derived from combinations of the α-amino acids.

4. Nitrosourea derivative selected from methyl 2'-[N-[N-(2-chloroethyl)-N-nitroso-carbamoyl]-glycyl]amino-2'-deoxy-α-D-glucopyranoside;

methyl 2'-[N-[N-(2-chloroethyl)-N-nitroso-carbamoyl]-β-alanyl]amino-2'-deoxy-α-D-glucopyranoside;

methyl 2'-[N-[N-(2-chloroethyl)-N-nitroso-carbamoyl]amino-n-butyryl]amino-2'-deoxy-α-D-glucopyranoside;

methyl 2'-[N-[N-(2-chloroethyl)-N-nitroso-carbamoyl]-L-alanyl]amino-2'-deoxy-α-D-glucopyranoside;

methyl 3'-[N-[N-(2-chloroethyl)-N-nitroso-carbamoyl]-glycyl]amino-3'-deoxy-α-D-mannopyranoside;

methyl 3'-[N-[N-(2-chloroethyl)-N-nitroso-carbamoyl]-glycyl]amino-3'-deoxy-α-D-glucopyranoside;

methyl 2'-[N-[N-(2-chloroethyl)-N-nitroso-carbamoyl]-L-seryl]amino-2'-deoxy-α-D-glucopyranoside;

1'-[N-[N-(2-chloroethyl)-N-nitroso-carbamoyl]-glycyl]amino-1'-deoxy-β-D-glucopyranose;

methyl 2'-[[N-[N-(2-chloroethyl)-N-nitroso-carbamoyl]-glycyl]-glycyl]amino-2'-deoxy-α-D-glucopyranoside;

methyl 2'-[N-[N-(2-chloroethyl)-N-nitroso-carbamoyl]-D-alanyl]amino-2'-deoxy-α-D-glucopyranoside;

2'[N-[N-(2-chloroethyl)-N-nitroso-carbamoyl]-glycyl]amino-2'-deoxy-D-glucopyranose;

methyl 6'-[N-[N-(2-chloroethyl)-N-nitroso-carbamoyl]-glycyl]amino-6'-deoxy-α-D-glucopyranoside;

1'-[N-[N-(2-chloroethyl)-N-nitroso-carbamoyl]-β-alanyl]amino-1'-deoxy-β-D-glucopyranose; and 1'-[N-[N-(2-chloroethyl)-N-nitroso-carbamoyl]amino-n-butyryl]amino-1'-deoxy-β-D-glucopyranose.

5. A pharmaceutical composition for the treatment of L 1210 leukemia comprising a therapeutically effective anti-leukemic amount of a nitrosourea derivative of formula (I):

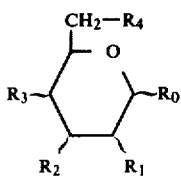 (I)

wherein $R_o$ represents —OH or —$OC_mH_{2m+1}$ where m is an integer of 1 to 3 and one of $R_1$, $R_2$, $R_3$ and $R_4$ represents

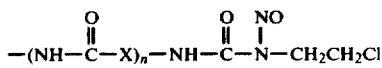

where X is

or an alkylene group of 1 to 3 carbon atoms, n is an integer of 1 to 3 and Y is the group on the α-carbon atom of an α-amino acid and each of the remaining three represents —OH; or wherein $R_o$ represents

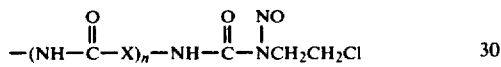

and $R_1$, $R_2$, $R_3$ and $R_4$ each represent —OH; in association with a pharmaceutically acceptable excipient, carrier or diluent.

6. A method for the therapeutic treatment of L 1210 leukemia which comprises administering an antileukemic effective amount, at suitable intervals, of a nitrosourea derivative of formula (I):

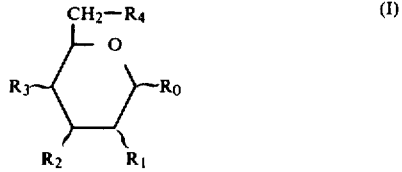 (I)

wherein $R_o$ represents —OH or —$OC_mH_{2m+1}$ where m is an integer of 1 to 3 and one of $R_1$, $R_2$, $R_3$ and $R_4$ represents

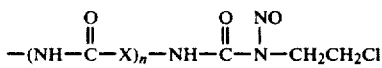

where X is

or an alkylene group of 1 to 3 carbon atoms, n is an integer of 1 to 3 and Y is the group on the α-carbon atom of an α-amino acid and each of the remaining three represents —OH; or wherein $R_o$ represents

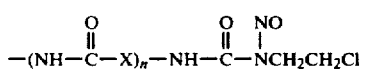

and $R_1$, $R_2$, $R_3$ and $R_4$ each represent —OH.

* * * * *